(12) United States Patent
Izumida et al.

(10) Patent No.: US 8,712,508 B2
(45) Date of Patent: Apr. 29, 2014

(54) STATE DETECTION DEVICE, ELECTRONIC APPARATUS, MEASUREMENT SYSTEM AND PROGRAM

(71) Applicant: Seiko Epson Corporation, Tokyo (JP)

(72) Inventors: Masamichi Izumida, Ryugasaki (JP); Masaki Gomi, Hino (JP)

(73) Assignee: Seiko Epson Corporation, Tokyo (JP)

( * ) Notice: Subject to any disclaimer, the term of this patent is extended or adjusted under 35 U.S.C. 154(b) by 0 days.

(21) Appl. No.: 13/793,741

(22) Filed: Mar. 11, 2013

(65) Prior Publication Data

US 2013/0245470 A1 Sep. 19, 2013

(30) Foreign Application Priority Data

Mar. 15, 2012 (JP) ................................. 2012-058204

(51) Int. Cl.
*A61B 5/04* (2006.01)
(52) U.S. Cl.
USPC ........................................................ 600/509
(58) Field of Classification Search
USPC ........................................................ 600/509
See application file for complete search history.

(56) References Cited

U.S. PATENT DOCUMENTS

| | | | |
|---|---|---|---|
| 5,788,655 A * | 8/1998 | Yoshimura et al. | 600/587 |
| 5,955,667 A | 9/1999 | Fyfe | |
| 6,135,951 A * | 10/2000 | Richardson et al. | 600/300 |
| 7,028,547 B2 | 4/2006 | Shiratori et al. | |
| 7,237,446 B2 | 7/2007 | Chan et al. | |
| 7,512,517 B2 | 3/2009 | Tsubata | |
| 7,747,411 B2 | 6/2010 | Kato | |

FOREIGN PATENT DOCUMENTS

| | | |
|---|---|---|
| JP | A-11-42220 | 2/1999 |
| JP | A-2002-263086 | 9/2002 |
| JP | A-2008-77368 | 4/2008 |
| JP | A-2008-84271 | 4/2008 |
| JP | A-2008-292294 | 12/2008 |
| JP | A-2011-177349 | 9/2011 |
| JP | A-2011-221798 | 11/2011 |
| WO | WO 2011/108372 A1 | 9/2011 |

* cited by examiner

*Primary Examiner* — George Manuel
(74) *Attorney, Agent, or Firm* — Oliff PLC

(57) ABSTRACT

A state detection device includes an acquisition part that acquires an acceleration detection value from an acceleration sensor, and a judgment part that judges a running state or a walking state based on the acceleration detection value. The judgment part detects as to whether a positive/negative sign of the acceleration detection value in a first axis reversed in a predetermined judgment period, determines the running state when the sign reverses, and determines the walking state when the sign does not reverse.

16 Claims, 13 Drawing Sheets

STATE DETECTION DEVICE, ELECTRONIC APPARATUS, MEASUREMENT SYSTEM AND PROGRAM

The present application claims a priority based on Japanese Patent Application No. 2012-058204 filed on Mar. 15, 2012, the contents of which are incorporated herein by reference.

BACKGROUND

1. Technical Field

The present invention relates to state detection devices, electronic apparatuses, measurement system and programs.

2. Related Art

Techniques for detecting the state of a user (for example, the state of exercise, etc.), with a device having various sensors attached to the body of the user, are widely used. Such devices include a heart rate monitor that detects user's heart rate information, a pedometer that estimates the number of steps while walking or running, etc.

Pedometers in recent years not only count the number of steps but also estimate other information such as the moving speed, the traveled distance, etc. of the user. It is desirable to estimate the state of the user (more concretely, as to whether the user is in the state of walking or running) in order to improve the accuracy in estimating the speed and the distance. This is because, for example, although it is necessary to use an appropriate value as the pace when the distance is calculated by the number of steps×the pace, the pace is different generally in the walking state and in the running state. This similarly applies when the speed, etc. are estimated by using parameters other than the pace. By switching the parameter in the walking state and in the parameter in the running state, an improvement in the accuracy of estimation results can be expected.

Moreover, the discrimination between the walking state and the running state is also effective in other cases besides the speed and the distance. For example, it is necessary to change the calculation method (for example, the calculation formula) depending on the load of exercise, in the case where the calorie consumption of the user is to be calculated.

In addition, because there are various processes where switching of the content is desirable between the walking state and the running state, there are strong demand for accurately judging the state of walking or running.

There have been devices that allow the user to input information to indicate whether the user is in the walking state or in the running state. However, there is a problem in view of the user's convenience as the input is needed when the user changes the state of movement. Accordingly, in recent years, automatic judgment systems are used to automatically judge the state of movement.

For example, according to JP-A-2011-221798 (Patent Document 1), the walking state or the running state is judged by measuring the time interval of pulse signals that correspond to steps in walking or in running. Also, according to JP-A-2008-077368 (Patent Document 2), when processing pulses corresponding to steps, a filter that can pass different frequency bands is used, thereby discriminating walking that is to be detected with a lower frequency from running that is to be detected with a higher frequency.

The methods described in Patent Document 1 and Patent Document 2 are both based on the idea that the time interval of the steps in the running state is longer than that in the walking state. However, the pitch in walking and running greatly differs from one person to another. There could be cases where the time interval between the steps is very short even in the walking state (race-walk, as an extreme example), or where the time interval between the steps is relatively long even in the running state (for example, the stride-running technique). Therefore, there is a danger of misjudgment in the techniques that are based on the time interval in the steps.

SUMMARY

In accordance with some aspects of the invention, state detection devices, electronic apparatuses, measurement systems and programs, that appropriately judge the walking state and the running state, based on an acceleration detection value from an acceleration sensor, can be provided.

An embodiment of the invention pertains to a state detection device including an acquisition part that acquires an acceleration detection value from an acceleration sensor, and a judgment part that judges a running state or a walking state based on the acceleration detection value. The judgment part detects as to whether a positive or negative sign of the acceleration detection value in a first axis reversed in a predetermined judgment period. When the sign reversed, the judgment part determines the running state, and when the sign did not reverse, the judgment part determines the walking state.

In the embodiment of the invention, when judging the running state or the walking state based on the acceleration detection value from the acceleration sensor, a processing is executed based on whether the positive or negative sign of the acceleration detection value in the first axis has reversed. As a result, judgment can be made by a simple processing, and the accuracy of judgment can be improved, compared with the technique that uses the pitch (step frequency).

Further, in accordance with an aspect of the embodiment, the judgment part may judge the running state or the walking state based on the acceleration detection value in an axis in a direction corresponding to the direction of gravity set as the first axis.

By this, judgment based on the direction of gravity becomes possible.

In accordance with an aspect of the embodiment, the judgment part may judge if the sign corresponding to the direction of gravity in the first axis is positive or negative based on the acceleration detection value in the first axis. When the acceleration detection value in the first axis with the sign different from the sign corresponding to the direction of gravity is detected at least once in the predetermined judgment period, the judgment part may determine the running state.

As a result, the positive or negative sign corresponding to the direction of gravity can be detected, and judgment can be made based on whether a value having a sign different from the sign has been detected.

Furthermore, in accordance with another aspect of the embodiment, when the sign of the acceleration detection value in the first axis in a first period within the predetermined judgment period is positive, and the sign of the acceleration detection value in the first axis in a second period following the first period within the predetermined judgment period is negative, or when the sign of the acceleration detection value in the first axis in the first period is negative, and the sign of the acceleration detection value in the first axis in the second period is positive, the judgment part may determine the running state.

As a result, reversal of the positive sign to the negative sign and vice versa can be detected, based on whether both a positive period and a negative period are present during the predetermined judgment period.

Also, in accordance with another aspect of the embodiment, the judgment part may determine the running state or the walking state based on the acceleration detection value in a period longer than the length of one step in walking or running set as the predetermined judgment period.

Accordingly, the judgment period can be set based on the length of one step, so that misjudgment can be suppressed.

Further, in accordance with an aspect of the embodiment, the state detection device may include a speed information calculation part that calculates speed information in the walking state or the running state based on the acceleration detection value.

As a result, calculation of speed information, together with judgment of the walking state or the running state, becomes possible.

Also, in accordance with an aspect of the embodiment, the speed information calculation part may calculate the speed information T by T=aS+b, where S is an average value of magnitudes of the acceleration detection values, and a and b are parameters for speed information calculation.

As a result, the accuracy in speed assumption, etc. can be improved, compared with the technique that uses the number of steps, because processing can be performed based on an average value of the acceleration detection values.

Moreover, in accordance with an aspect of the embodiment, the speed information calculation part may calculate the speed information r by r=cI$^2$+dI+e, where I is an integrated value of values corresponding to absolute values of the acceleration detection values in at least one coordinate axis component, and c, d and e are parameters for speed information calculation.

As a result, the accuracy in speed assumption, etc. can be improved, compared with the technique that uses the number of steps, because processing can be performed based on an integrated value of the acceleration detection values.

Further, in accordance with an aspect of the embodiment, the speed information calculation part may calculate the speed information based on angle information θ that corresponds to an angle defined by a first acceleration vector expressing the acceleration detection value at a first timing and a second acceleration vector expressing the acceleration detection value at a second timing, and a speed information calculation parameter.

As a result, the accuracy in speed assumption, etc. can be improved, compared with the technique that uses the number of steps, because processing based on angle information of acceleration vectors which express the acceleration detection value can be conducted.

Furthermore, in accordance with an aspect of the embodiment, the speed information calculation part may calculate the speed information V by V=m θ$_{sum}$+n, where θ$_{sum}$ is an integrated value of the angle information θ, and m and n are the speed information calculation parameters.

Accordingly, processing based on an integrated value of angle information becomes possible.

Also, in accordance with an aspect of the embodiment, the speed information calculation part may set a parameter for running as the speed information calculation parameter when the running state is determined by the judgment part, and may set a parameter for walking as the speed information calculation parameter when the walking state is determined by the judgment part.

As a result, appropriate speed information according to the state of exercise can be calculated, because the parameter to be used to calculate the speed information can be switched based on the result of judgment of the walking state or the running state.

Also, in accordance with an aspect of the embodiment, the state detection device may include a distance information calculation part that calculates moved distance information in the walking state or the running state based on the speed information calculated by the speed information calculation part.

As a result, calculation of distance information, in addition to judgment of the walking state or the running state, becomes possible.

Another embodiment of the invention pertains to an electronic apparatus that includes the state detection device and the acceleration sensor described above.

In accordance with an aspect of the embodiment of the invention, the electronic apparatus includes a plurality of terminals used for detection of heart rate and for attachment of the electronic apparatus to the chest of a body to be examined. The acceleration sensor may be a three-axis acceleration sensor that acquires the acceleration detection values along three axes of X axis, Y axis and Z axis that are orthogonal to one another. When the electronic equipment is affixed to the body to be examined with the plural terminals, the direction in the Z axis assumes a direction corresponding to the traveling direction in the walking state or the running state. The judgment part may judge the running state or the walking state based on the acceleration detection value in the Y axis.

Accordingly, the processing load can be reduced, because the coordinate axis used for judgment of the walking state or the running state can be decided in advance when the electronic equipment is used as a heart rate monitor.

Also, another embodiment of the invention pertains to a measurement system including the state detection device described above.

Moreover, another embodiment of the invention pertains to a program that renders a computer to function as an acquisition part that acquires an acceleration detection value from an acceleration sensor, and a judgment part that judges a running state or a walking state based on the acceleration detection value. The judgment part detects as to whether a positive/negative sign of the acceleration detection value in a first axis reversed in a predetermined judgment period. When the sign reversed, the judgment part determines the running state, and when the sign did not reverse, the judgment part determines the walking state.

DESCRIPTION OF EXPLANATORY EMBODIMENTS

Figure 1A:
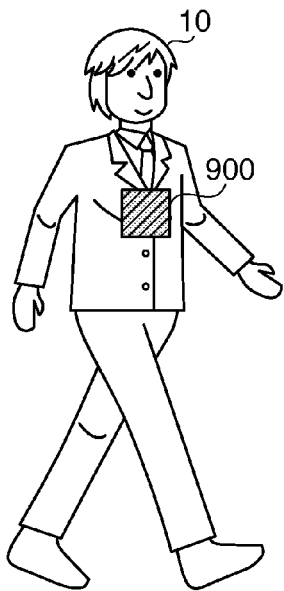
FIG. 1A shows an example in which an electronic equipment in accordance with an embodiment is mounted on the user's chest.

Embodiments of the invention are described below. It is noted that the embodiments described below do not unduly limit the contents of the invention set forth in the scope of patent claims. Also, not all of the compositions described in the embodiments would necessarily be essential components.

1. Method in Accordance with Embodiment

A method in accordance with an embodiment of the invention will be described first. As a method for detecting the state (in particular, walking state and running state) of the user, a method that detects the state based on sensor information from a sensor (in particular, an acceleration sensor) attached to the user is known.

For instance, by a device for measuring the number of steps such as a pedometer, it is possible to estimate the moving speed and the moved distance during walking or running based on the number of steps detected. For example, the distance and the speed may be obtained by formulas, such as, for example, the distance=the number of steps×the pace, and the speed=the distance/the time required. However, it is readily understood that the moved distance and the speed become different depending on whether the user is walking or running, even when the number of steps is exactly the same. In other words, accurate estimation of the speed, etc. is difficult unless the value of the pace is appropriately switched according to the state of movement.

Even when the speed, etc. are estimated based on other values without depending on the number of steps (for example, based on acceleration detection values from an acceleration sensor, changes in acceleration vector angle or the like, as described later), an improvement in the estimation accuracy can be expected by changing the parameter, etc. used for the estimation. Additionally, even in processings other than the processing in the pedometer, there are many cases where judgment of the walking state and the running state is effective.

However, the technique, that has been used widely in the past, is based on assumption that the time interval in the steps is longer (or, the step frequency is lower) in the walking state than in the running state. However, the time interval in the steps at the time of walking is different from one user to another. In addition, the time interval in the steps in running differs greatly depending on whether the user likes the pitch running method or the stride running method (or, depending on the ground condition or the like even in the case of the same user). In other words, it is difficult to clearly set a threshold to divide between walking and running, with respect to the time interval in the steps or the step frequency, and the danger of misjudgment cannot be negated.

In view of the above, the inventor of the present application proposes a method and a process for judging walking or running which does not depend on the time interval in the steps. More specifically, the process is executed based on the fact (this is not assumption) that there is a moment when neither of the feet is placed on the ground in the running state between landing of one foot on the ground and landing of the other foot on the ground, on the other hand, at least one of the right foot and the left foot is placed on the ground without fail at any time in the walking state.

In other words, acceleration in an opposite direction of the direction of gravity appears in one step in the running state, as the feet come off the ground, defying the gravity. In contrast, such a situation does not occur in the walking state. In accordance with an embodiment of the invention, walking or running judgment is performed based on whether or not acceleration in the opposite direction of the direction of gravity has been detected.

More specifically, the coordinate axis corresponding to the direction of gravity (which may coincide with the direction of gravity, without any limitation thereto, and details thereof will be described later) is considered, and the judgment processing may be executed based on the sign of a component of the coordinate axis of an acceleration detection value provided from the acceleration sensor. Note that the acceleration detection value is a value represented by sensor information provided from the acceleration sensor, and when the acceleration sensor has one axis, it is a scalar that expresses an acceleration value in the axis concerned. However, an acceleration sensor generally has N axes (where N is an integer of 2 or more, for example, N=3), and the acceleration detection value in this case is an N-dimensional vector. Hereafter, when the description below refers to an "acceleration detection value in a given coordinate axis" or the like, it is assumed to express a component (a scalar amount) corresponding to the axis concerned among the N-dimensional vector components. However, the "given coordinate axis" is not limited to the axis in the coordinate system set to the acceleration sensor, but may indicate a coordinate axis included in the coordinate system after conversion, when a coordinate conversion processing is performed. When such a term as an "acceleration detection value" is used without limiting to a coordinate axis, it is assumed to express in principle an N-dimensional vector or N scalar amounts, but it is not limited to such definition when the subject coordinate axis being discussed is clear in the context.

In the acceleration detection value in the coordinate axis corresponding to the direction of gravity, a component corresponding to the gravitational acceleration is predominant (which is very large compared to noise or signals caused by user's movements). Therefore, acceleration in the opposite direction of the direction of gravity is detected based on the change in the sign of the component in the coordinate axis of the acceleration detection value, thereby judging walking or running from the detection result.

Figure 2A:
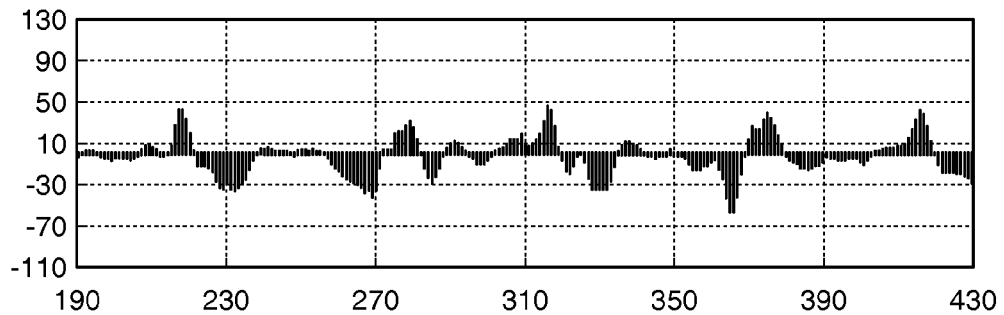
FIGS. 2A-2D are examples of acceleration detection values in the walking state.
Figure 2B:
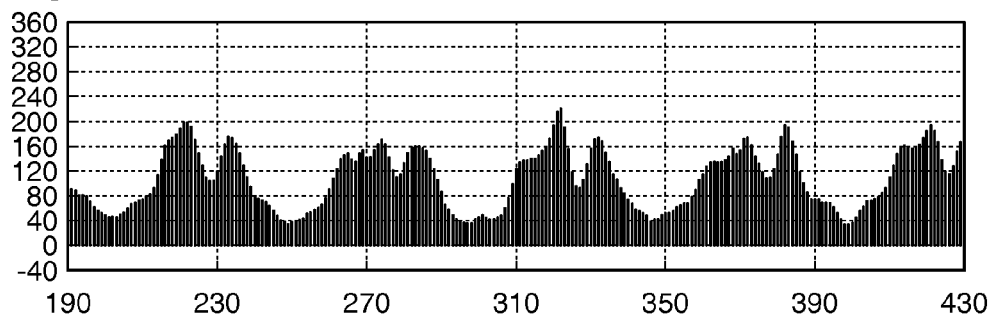
Figure 2C:
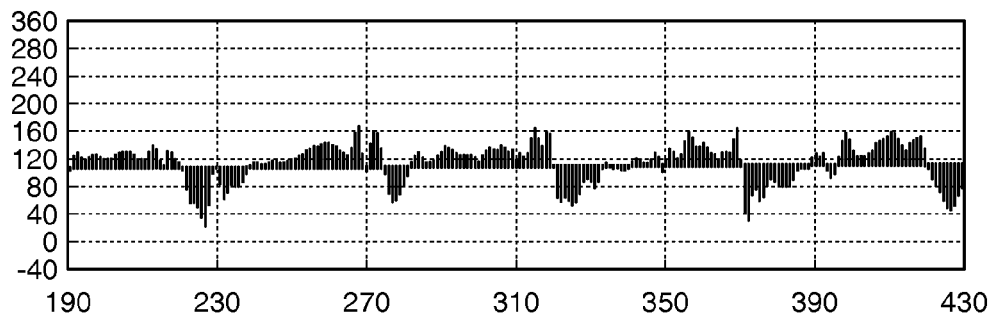
Figure 2D:
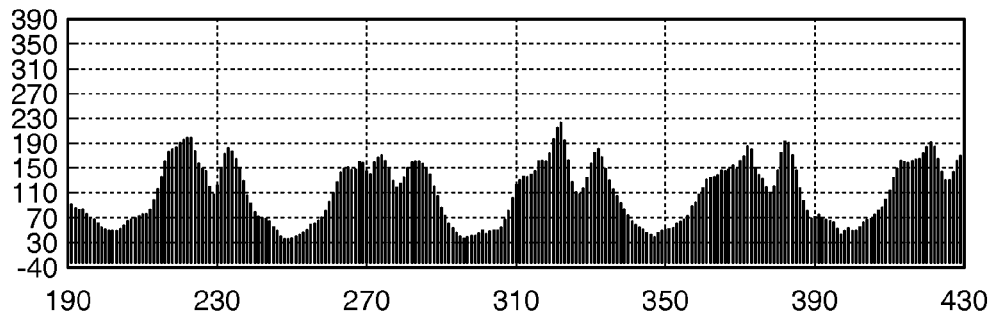

Examples of measured values in the walking state are shown in FIGS. 2A-2D, and examples of measured values in the running state are shown in FIGS. 3A-3D. FIG. 2A, FIG. 2B and FIG. 2C show changes with time of X-axis component, Y-axis component, and Z-axis component of the acceleration detection value, respectively, and FIG. 2D shows changes with time of a resultant acceleration (for example, a root-sum-square) in the three axes. This similarly applies to the running state.

Each of the axes X, Y, and Z is assumed to be the one shown in FIG. 5A to be described below. The components in the Z-axis and the X-axis that are in the horizontal direction (i.e., the traveling direction or a direction orthogonal thereto) would likely be influenced by signals caused by staggering of the user, etc. because their signal values generated by walking or running are small, and therefore are unsuitable to judgment of the state. Moreover, a resultant acceleration always becomes non-negative, and therefore is not used in the method of the embodiment. Therefore, the coordinate axis to be used for the processing of the embodiment is an axis corresponding to the direction of gravity indicated in FIG. 2B and FIG. 3B (i.e., the Y-axis in this example). The difference of the acceleration detection value in the Y-axis between the walking state and the running state is clear from FIG. 2B and FIG. 3B. That is, while the sign does not reverse in the walking state (it is always positive here), the sign reverses in the running state (positive values are predominant but negative values also appear here). The method of the embodiment judges the state walking or running based on this difference.

Figure 4:
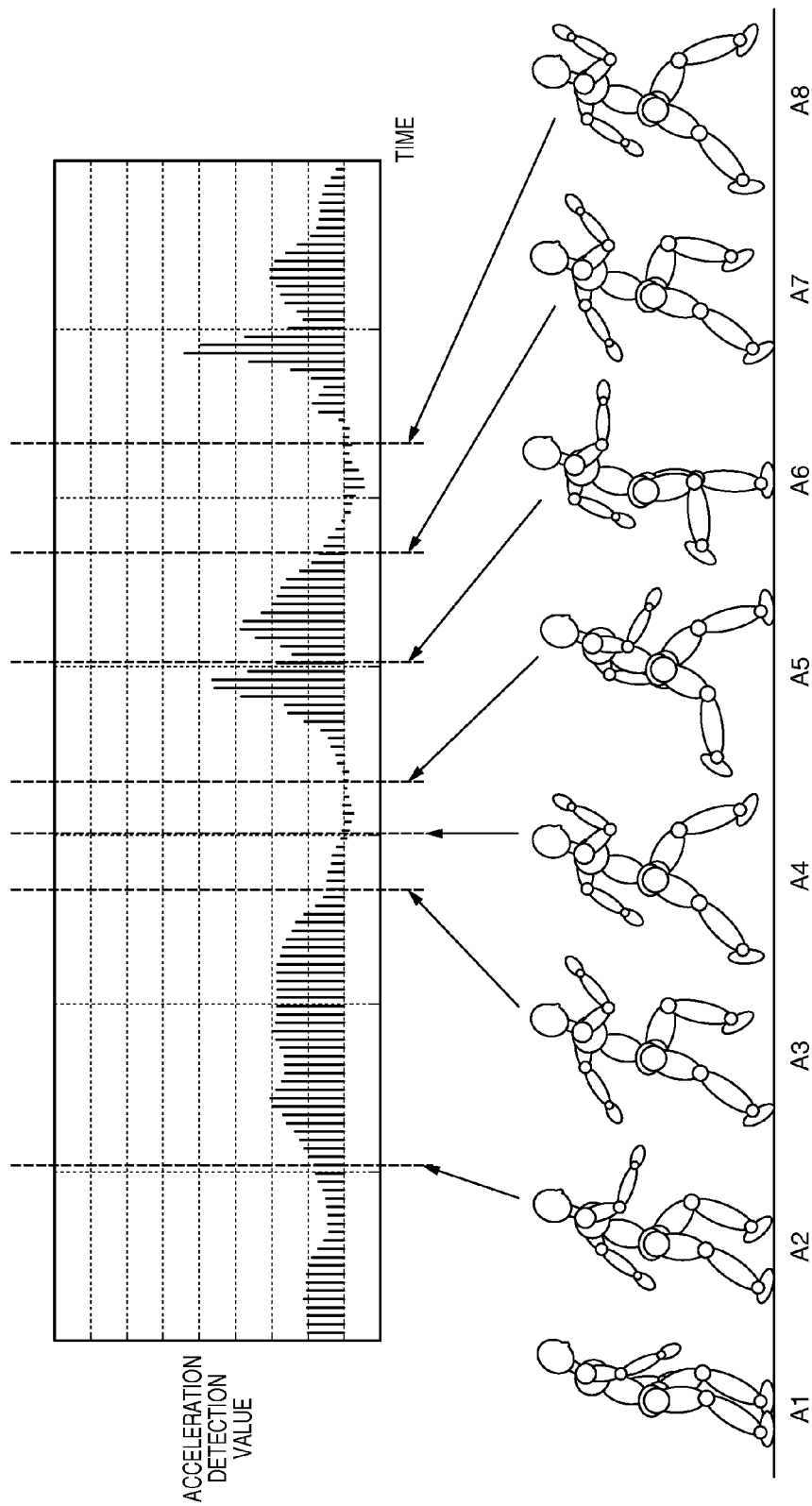
FIG. 4 is an illustration for explaining the correspondence between movements of the user in the running state and acceleration detection values.

Changes with time of the axis component corresponding to the direction of gravity of the acceleration detection value in the running state correlated with user's movements are shown in FIG. 4. As shown in A1-A8 of FIG. 4, in the running state, the body first sinks and the right leg starts stepping and pushing up the body (A1). Then, the body inclines forward and thrusting forward of the body by the right leg begins (A2), and the user's right leg starts coming off the ground corresponding to the ending timing of thrusting forward by the right leg (A3). Then, after passing a period when both of the feet are not on ground (A4), the left leg lands on the ground (A5). After advancing the body forward by the left leg and swinging the right leg forward (A6), the thrusting of the body forward by the left leg ends, and the left leg starts leaving the ground (A7). A period in which both of the feet are not on the ground starts again similarly to A4, except that the foot swung forward is different in A8.

As shown in the graph of FIG. 4, the acceleration detection value will have periodicity corresponding to the periodic movements such as A1-A8, the signal value becomes small at the timing of A3, and assumes a negative value around a period corresponding to A4-A5. After the signal value increases from A5 through A6 once, the signal value changes to a decrease again and assumes a negative value around a period corresponding to A7-A8. In other words, during one step (for example, from landing of one foot on the ground to landing of the other foot on the ground) in the running state, the signal value assumes a negative value once (in a broad sense, a value with a sign different from the sign corresponding to gravitational acceleration).

Hereafter, an example of a system configuration as a state detection device and an electronic apparatus including the state detection device will be first described, and thereafter a concrete example of the walking or running judgment method based on acceleration detection values will be described. Here, a processing for setting coordinate axes to be used for judgment is described first, and then two methods of processing after the coordinates axes have been set will be described. Furthermore, in consideration of a case where the method of the present embodiment is combined with a speed assumption method using an acceleration sensor (for example, when realizing a pedometer and the like that executes both of the methods), the speed assumption method will also be described. Various parameters used in the speed assumption method may be switched to different parameters in the walking state and in the running state.

2. System Configuration Example of State Detection Device, ETC.

FIG. 1A shows an example in which the user 10 wears an electronic apparatus 900 including a state detection device in accordance with an embodiment of the invention on the chest. It is noted that the electronic apparatus 900, though put on the chest in FIG. 1A, may be installed at any position other than the chest. For example, by installing the electronic apparatus 900 on a portion with a large movement at the time of walking and running, such as the hand or the foot of the user 10, the signal value of the sensor information can be made greater compared with installing it on the chest.

Figure 1B:
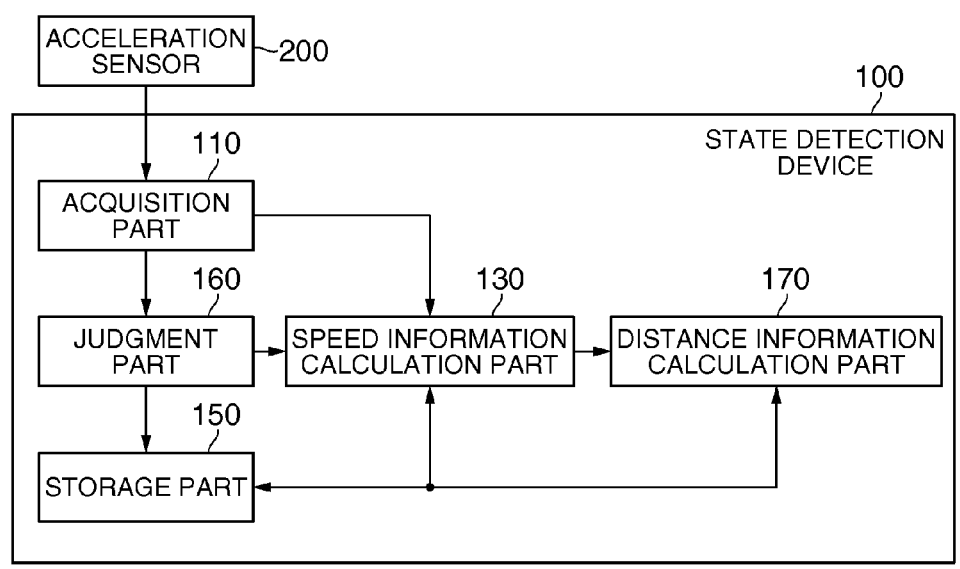
FIG. 1B is a configuration example of a state detection device in accordance with the present embodiment.

Next, a detailed configuration example of the state detection device 100 of the embodiment and the electronic apparatus 900 (or a measurement system) including the state detection device 100 is shown in FIG. 1B.

The state detection device 100 includes an acquisition part 110, a speed information calculation part 130, a storage part 150, a judgment part 160, and a distance information calculation part 170. As examples of the electronic apparatus 900 including the state detection device 100, an acceleration sensor 200, a pedometer that includes an antenna part 300, a wireless communication part 400, etc. shown in FIG. 5A to be described below may be enumerated. It is noted that the state detection device 100 and the electronic apparatus 900 including the state detection device 100 are not limited to the configuration shown in FIG. 1B, and various modifications can be made. For example, a part of the components thereof may be omitted, or other components (for example, a calibration processing part that performs calibration processing for the speed information operation or the like) may be added. Moreover, a part or all of the functions of the state detection device 100 of the present embodiment may be realized by a server connected through the antenna part 300, the wireless communication part 400 and a communication system.

The acquisition part 110 acquires an acceleration detection value from the acceleration sensor 200. The acquisition part 110 is an interface part to communicate with the acceleration sensor 200, and may use a bus or the like.

The speed information calculation part 130 calculates speed information based on the acceleration detection value. The speed information may be the speed itself, or may be information to obtain the speed (for example, a scale factor with respect to a reference value of the speed).

The storage part 150 stores parameters such as coefficients and the like to be used to obtain speed information, and provides a work area for each of the parts. The function of the storage part 150 may be achieved by a memory such as a RAM and a HDD (Hard Disk Drive).

The judgment part 160 judges the user's movement. More specifically, the judgment part 160 judges the walking state or the running state based on the sign of the coordinate axis component of the acceleration detection value. Details of the judgment process will be described later.

The distance information calculation part 170 calculates distance information indicative of the moved distance of the user associated with walking or running. The distance information may be the distance itself, or may be information to obtain the distance (for example, a scale factor with respect to a reference value of the moved distance).

Note that the acquisition part 110, the speed information calculation part 130, the judgment part 160, and the distance information calculation part 170 can be achieved by hardware, such as, various processors (CPU, etc.) and ASIC (gate array, etc.), and programs.

Further, the acceleration sensor 200 may be composed of an element whose resistance value increases or decreases by an external force, and detects acceleration information in three axes. However, the number of axes of the acceleration sensors 200 of the embodiment is not limited to three axes.

Figure 5A:
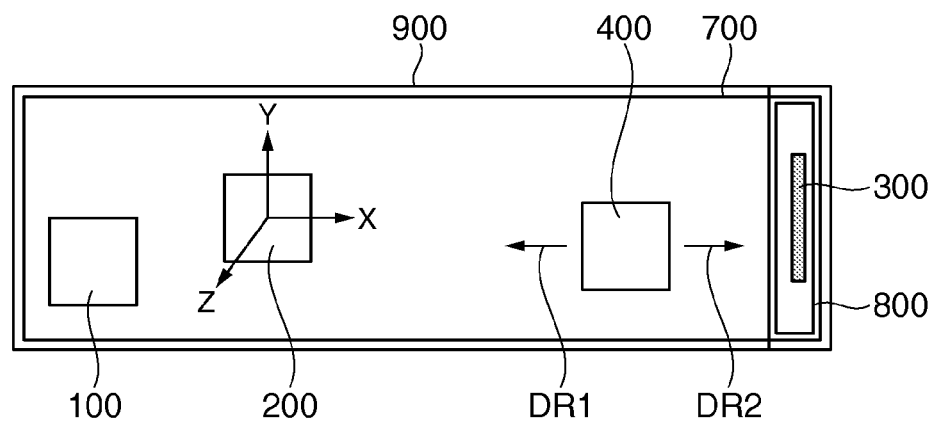
FIGS. 5A and 5B are examples of hardware configurations of electronic equipment in accordance with an embodiment.
Figure 5B:
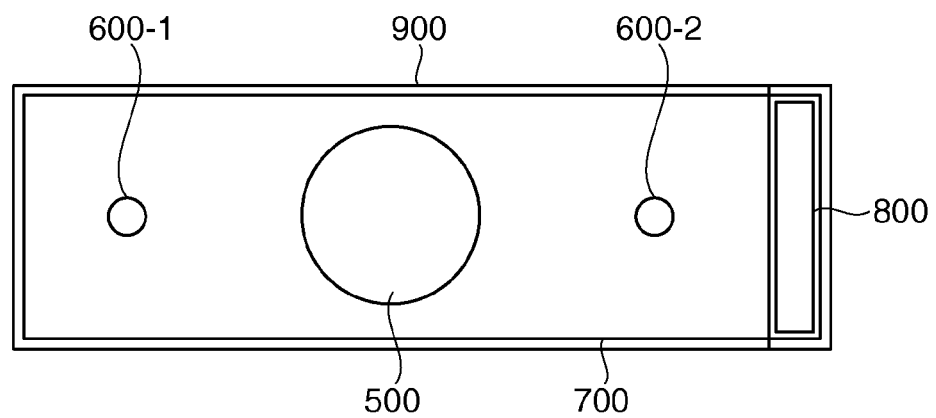

Next, an example of the hardware configuration of the electronic apparatus 900 is described by using FIG. 5A and FIG. 5B. FIG. 5A shows the top surface of a first electronic substrate 700 included in the electronic apparatus 900, and FIG. 5B shows the back surface of the first electronic substrate 700. To avoid confusion in the illustration, a frame that shows the first electronic substrate 700 is illustrated being separated from a frame that shows the electronic apparatus 900 in FIG. 5A and FIG. 5B. However, they actually coincide with each other. This similarly applies to a second electronic substrate 800 to be described later.

First, the electronic apparatus 900 of the embodiment may include a state detection device 100, an acceleration sensor 200, a wireless communication part 400, an antenna part 300, and a battery 500 (a battery socket).

However, the electronic apparatus 900 is not limited to the configuration shown in FIG. 5A and FIG. 5B, and various modifications can be made. For example, omission of a part of these components and addition of other components are possible. For example, the electronic apparatus 900 may include heart rate measurement electrode terminals shown at 600-1 and 600-2 of FIG. 5B, in case the electronic apparatus 900 is formed from a pedometer and a heart rate monitor in combination. In this case, the two heart rate measurement electrode terminals 600-1 and 600-2 are installed in a position where the heart is located between them.

Here, the wireless communication part 400 controls communications between the state detection device 100 and the antenna part 300. The wireless communication part 400 can be realized by hardware, such as, various processors (CPU, etc.) and ASIC (gate array, etc.) and programs.

Moreover, the antenna part 300 is a device that radiates (transmits) high frequency energy as electric wave (electromagnetic radiation) in the space or, conversely, converts (receives) electric wave (electromagnetic radiation) in the space into high frequency energy. Note that the antenna part 300 of the embodiment at least has a transmission function. In addition, a single antenna part 300 or a plurality of antenna parts 300 may be installed for the electronic apparatus 900. For example, when a plurality of antenna parts 300 are installed, each of the antenna parts may have a different caliber.

However, when the acceleration sensor 200 and the antenna part 300 are mounted on the same substrate, an error may be caused in the detection result of the acceleration sensor 200 due to influence by the electric wave (electromagnetic radiation) emitted from the antenna part 300. For this reason, in the past, the acceleration sensor 200 and the antenna part 300 are separated and mounted on independent substrates, respectively, to prevent errors from occurring in the detection result of the acceleration sensor 200. However, in such a case, the electronic apparatus 900 becomes large due to the combined thickness of the substrates, which leads to a problem in that, the electronic apparatus 900, if installed on the chest or the like during exercise, would interfere with the exercise.

Therefore, in accordance with the embodiment as shown in FIG. 5A and FIG. 5B, the state detection device 100, the acceleration sensor 200, the wireless communication part 400, and the battery 500 are mounted on the first electronic substrate 700, and the acceleration sensor 200 may be mounted on a first direction DR1 side of the wireless communication part 400, and the antenna part 300 may be mounted on a second direction DR2 side of the wireless communication part 400.

As a result, the acceleration sensor 200 and the antenna part 300 can be mounted, separated from each other, which makes it more difficult for errors, which may be caused by electric wave emitted from the antenna part 300, to occur in the detection result of the acceleration sensor 200. However, as it only requires mounting the acceleration sensor 200 and the antenna part 300 separated from each other, various changes can be made, such as, switching the directions DR1 and DR2, and the like.

In addition, by mounting the state detection device 100, the acceleration sensor 200, the wireless Communication part 400, the antenna part 300, and the battery 500 on a single substrate, the electronic apparatus 900 can be made more compact. As a result, the electronic apparatus 900, even when installed on the chest, etc. in exercise, would not hinder the exercise.

Moreover, in the electronic apparatus 900, the antenna part 300 may be mounted on the second electronic substrate 800 that is installed in the first direction side of the wireless communication part 400.

It is preferable to exclude a substrate pattern on the back surface of the second electronic substrate 800. Moreover, the second electronic substrate 800 may preferably be disposed on the first electronic substrate 700, superposed along its edge, as shown in FIG. 5A and FIG. 5B. However, without any limitation to the above, for example, only a part of the first electronic substrate 700 may be superposed on the second electronic substrate 800.

As a result, the acceleration sensor 200 and the antenna part 300 can be separated farther from each other and mounted, which makes it even more difficult for errors, which may be caused by electric wave emitted from the antenna 300, to occur in the detection result of the acceleration sensor 200.

Moreover, in the electronic apparatus 900, the state detection device 100, the acceleration sensor 200, and the wireless communication part 400 may be mounted on the top surface of the first electronic substrate 700, and the battery 500 may be mounted on the back surface of the first electronic substrate 700.

As a result, the electronic apparatus 900 can be made much thinner.

3. Walking or Running Judgment Based on Acceleration Detection Value

Next, a method of conducting a walking or running judgment based on acceleration detection values will be described. A method of setting a coordinate axis to be used for the judgment will be described first, and then two methods of judgment based on the coordinate axis component of the acceleration detection value will be described.

3.1 Setting of Coordinate Axis Corresponding to the Direction of Gravity

As described above, in the walking or running judgment in accordance with the embodiment, the direction of gravity is considered as a reference, and the processing is executed based on whether acceleration in the opposite direction of the direction of gravity has been detected. The gravitational acceleration of 1G always works in the direction of gravity, and external turbulence, that originates from exercise, etc. of the user, is substantially small (for example, it is about 0.1G-0.2G, and it is hardly possible to exceed 0.3G), compared with the gravitational acceleration. Therefore, as the acceleration detection value in the coordinate axis set to match with the direction of gravity is predominantly made up of positive values because of the gravitational acceleration (+1G), it can be assumed that appearance of negative values is not triggered by noise, but rather by movements of the user, for example, when the user jumps up. Because the walking state or the running state is concerned here, the running state will be determined when a negative value appears.

However, the coordinate axis to be used for judging the state of walking or running in accordance with the embodiment only has to be able to distinguish if the change of the sign of the acceleration detection value in the coordinate axis is due to external turbulence such as noise, or if the change reflects actual running movement. In other words, if a component due to the gravitational acceleration in a coordinate axis is sufficiently large with respect to external disturbance components such as noise (in other words, if the noise margin is sufficiently large), then there will not be any problem in using the coordinate axis for the walking or running judgment in the embodiment, and therefore the coordinate axis is not limited to the one that coincides with the direction of gravity.

Figure 6:
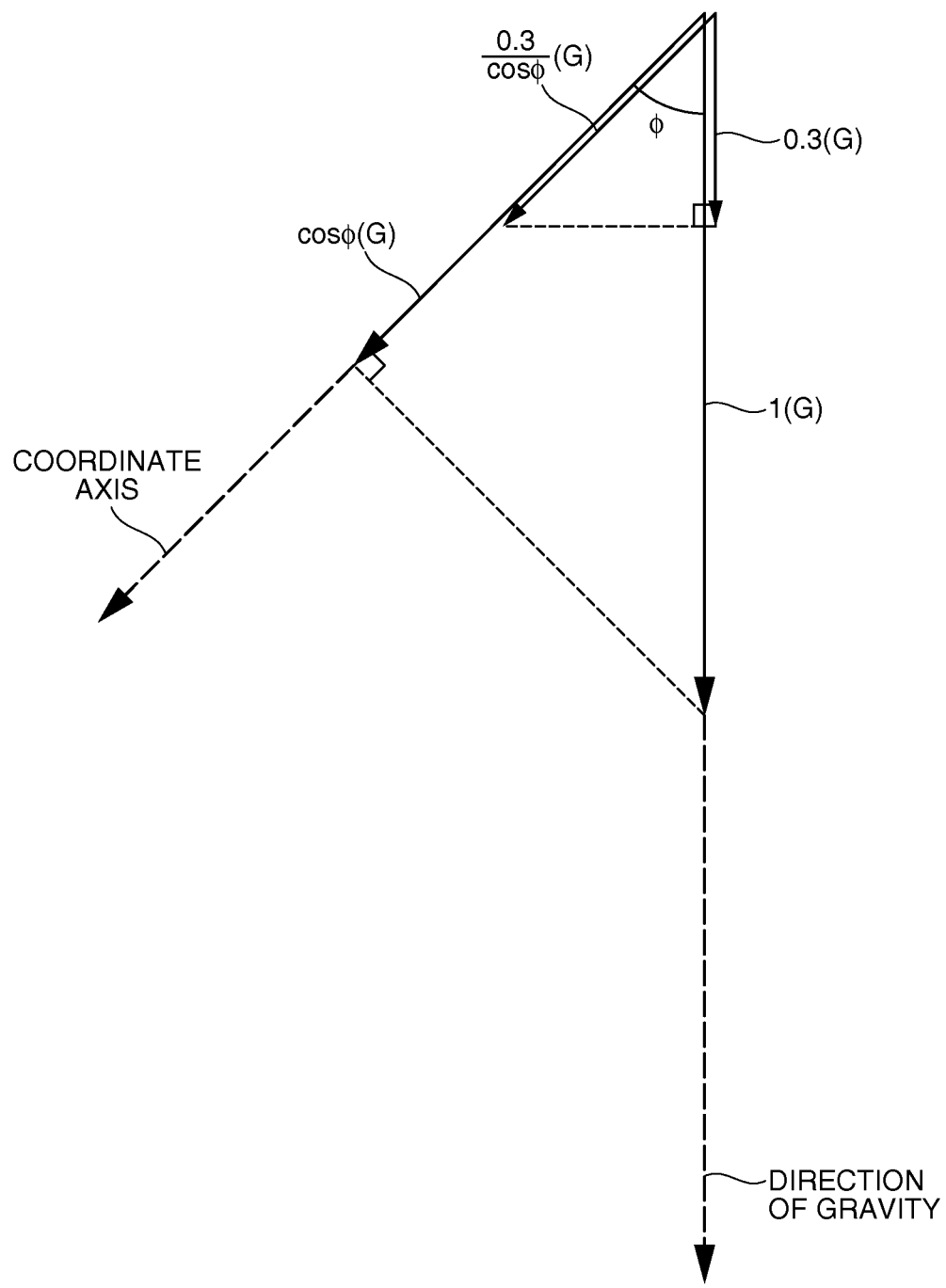
FIG. 6 shows the relation between coordinate axes used for a processing in accordance with an embodiment of the invention and the direction of gravity.

Accordingly, a coordinate axis whose angle defined with the direction of gravity is below a threshold value may also be used for the processing in accordance with the embodiment. An example is shown in FIG. 6. Although FIG. 6 illustrates the coordinate axes in a plane, the coordinate axes should be defined in the three-dimensional space, because the processing in a real space is necessary. As shown in FIG. 6, the gravitational acceleration of 1G and noise of about 0.3G (a value that is larger than an empirically obtained value is assumed) work in the direction of gravity. Though FIG. 6 shows a noise in the direction of gravity, the noise may also work in the opposite direction to the direction of gravity (varies within the range of about −0.3G to +0.3G).

Here, in the case of a coordinate axis whose angle defined with the direction of gravity is $\phi$, the coordinate axis component of the gravitational acceleration is $\cos\phi$(G). Also, the noise of 0.3G described above is a value empirically obtained as a result of the observation of the component in the direction of gravity. Therefore, the acceleration vector, which expresses the noise, may coincide or may not coincide with the direction of gravity, and when it does not coincide with the direction of gravity, a vector that is created by projecting the vector concerned to the direction of gravity has a magnitude of 0.3G. In other words, the possibility of detecting a noise greater than 0.3G cannot be denied, depending on the setting of the coordinate axis. When the acceleration vector that expresses noise coincides with the set coordinate axis, the noise to be detected in the concerned coordinate axis assumes the maximum value.

In other words, in the case of a coordinate axis whose angle defined with the direction of gravity is $\phi$, as shown in FIG. 6, it is necessary to consider the possibility that noise with the maximum magnitude of y(G) is generated, and y is given by the following expression (1).

[Expression 1]

$$y = \frac{0.3}{\cos\phi} \quad (1)$$

As a noise margin, a difference value between the component of the gravitational acceleration and the noise component needs to be considered. Therefore, when a coordinate axis coinciding with the direction of gravity is set, the noise margin becomes to be 1−0.3=0.7(G). Therefore, the noise margin nm in the coordinate axis whose angle defined with the direction of gravity is $\phi$ is given by the following expression (2).

[Expression 2]

$$nm = \cos\phi - \frac{0.3}{\cos\phi} \quad (2)$$

If $\phi$ does not make the value of nm to be at least a positive value, such a value of $\phi$ is not desirable to be set for a coordinate axis to be used in the processing of the present embodiment. Accordingly, if $\phi$ is decided on condition that nm is greater than 0 (nm>0), a value of about 57° can be set as $\phi$. However, in the present embodiment, a relatively larger value is given as nm, thereby securing the strength to turbulence. Specifically, $\phi$=45° is used, and a coordinate axis whose angle defined with the direction of gravity is 45° or less is set.

In the present embodiment, it only has to be able to detect the presence or absence of a component in the opposite direction of the component of the gravitational acceleration, and therefore the component of the gravitational acceleration does not need to appear in a positive direction of the coordinate axis. Therefore, the opposite direction of the direction of gravity may be set as a reference, and a coordinate axis whose angle defined with the direction is 45° or less may be set in this case. This corresponds to the case where the angle $\phi$ is 135° or more, when the range of the angle $\phi$ is considered to be between 0° and 180° with respect to the direction of gravity. In other words, the range of angle of 45° may be considered with respect to the direction of gravity and its opposite direction as reference, respectively, or the range of angle of 45° or less or 135° or more may be considered with respect to the direction of gravity alone as reference.

Acceleration detection values of the acceleration sensor are acquired as values in the coordinate system set to the sensor (hereafter, the sensor coordinate system). For example, in the case of a three-axis acceleration sensor, a coordinate system consisting of three mutually orthogonal axes becomes a sensor coordinate system. In other words, because it is possible to use the coordinate axis in the range of angle described above with respect to the direction of gravity in the processing, it can be assumed that at least one of the axes of the sensor coordinate system may be used for the processing in the present embodiment. In other words, a most suitable axis may be selected from among the sensor coordinate system, and acceleration detection values in the coordinate axis can be used for the processing as is, and the sensor coordinate system may not necessarily have to be transformed into a coordinate system for analysis of a walking or running judgment (hereafter, an analysis coordinate system).

Therefore, for example, when the degree of freedom in the installation attitude of the electronic apparatus 900 is very large, such as, when a smart phone equipped with the acceleration sensor 200 is used as the electronic apparatus 900 of the embodiment, it is sufficient if the coordinate axis selection processing is performed, and the coordinate transformation to an analysis coordinate system may not necessarily be performed.

In the example described above, the coordinate axis is set according to the angle with respect to the direction of gravity. However, the invention is not limited to such an example. This is because the processing load may increase depending on circumstances as the direction of gravity needs to be assumed so as to use the angle. Therefore, the coordinate axis to be used in the embodiment may be selected not based on the angle, but based on the acceleration detection value in each axis of the sensor coordinate system. More specifically, the component of the gravitational acceleration in each of the axes may be assumed based on the acceleration detection value, and the assumed value may be compared with a predetermined threshold. An axis whose value of the component of the gravitational acceleration is greater than the threshold value may be selected as a coordinate axis corresponding to the direction of gravity. As the threshold value, an ideal value given when assuming that the angle defined with the direction of gravity is 45° may be set, whereby a noise margin similar to the one obtained by the setting method based on the angle described above can be set. Then, the component of the gravitational acceleration in that case may be set with $\phi=45°$ in cos $\phi$ as shown in FIG. 6, and is given by $1/\sqrt{2}(G)$.

On the other hand, in the case of an electronic apparatus 900 that performs processings as a heart rate monitor, as shown in FIGS. 5A and 5B, in which the two heart rate measurement electrode terminals 600-1 and 600-2 need to be mounted at positions that interpose the heart, the degree of freedom in the installation attitude is small. For example, let us consider the case where connector portions 610-1 and 610-2 that also serve as electrodes are provided on a band 80 that is mounted on the chest, and an electronic apparatus 900 (a heart rate monitor) is fixed to the user 10 by connecting the electrodes 600-1 and 600-2 to the connector parts 610-1 and 610-2. In this case, it only has to consider two installation attitudes, a first installation attitude in which 600-1 is connected with 610-1 and 600-2 is connected with 610-2, and a second installation attitude in which 600-1 is connected with 610-2 and 600-2 is connected with 610-1. The second installation attitude is reverse with respect to the first installation attitude by 180° in a vertical direction. In this case, by making one axis of the sensor coordinate system correspond to the direction of gravity (or, the opposite direction) in the first installation attitude as shown in FIG. 5A, the axis will correspond to the opposite direction of the direction of gravity (or, the direction of gravity) even if the apparatus is installed in the second installation attitude. In other words, in the case where the degree of freedom in the installation attitude is low like this, the coordinate axis to be used for the walking or running judgment is defined at the stage of designing the apparatus, and it is even possible to provide a composition that does not need even the selection processing.

In the examples described above, the coordinate axis to be used for the processing is selected from among the sensor coordinate system based on the angle or the acceleration detection value, and the coordinate axis is defined at the time of designing. However the invention is not limited to the examples. For example, a coordinate transformation processing may be carried out to transform a sensor coordinate system to an analysis coordinate system, and one of the axes of the analysis coordinate system after conversion may be made to correspond to the direction of gravity.

When the coordinate transformation is performed, the processing load becomes heavy, compared with the case where the coordinate transformation is not performed, which is undesirable. However, it can be assumed that the coordinate transformation processing may be performed based on the direction of gravity in another example of processings, such as, an embodiment of speed information calculation to be described later. In such a case, because the processing load would not increase in the system as a whole, even if coordinate transformation is performed in the walking or running judgment, one of the axes of the analysis coordinate system may set as a coordinate axis to be used for the processing. Even in this case, the selected coordinate axis is not limited to the one corresponding to the direction of gravity, and deviations to the extent that the condition described above is met are allowed.

3.2 First Method

A method of judging the walking state or the running state will be concretely described. In a first method, whether a component of the gravitational acceleration in a coordinate axis set appears in a positive direction or appears in a negative direction is detected. In the aforementioned method, as the coordinate axis to be used for the judgment, not only the direction of gravity (and, an axis with a deviation with respect to the direction of gravity satisfying the condition), but also the opposite direction of the direction of gravity (and, an axis with a deviation with respect thereto satisfying the condition) are allowed to be set. Therefore, although it is understood that the component of the gravitational acceleration is predominant in the acceleration detection value in the axis, whether the sign thereof is positive or negative is not defined.

Figure 3A:
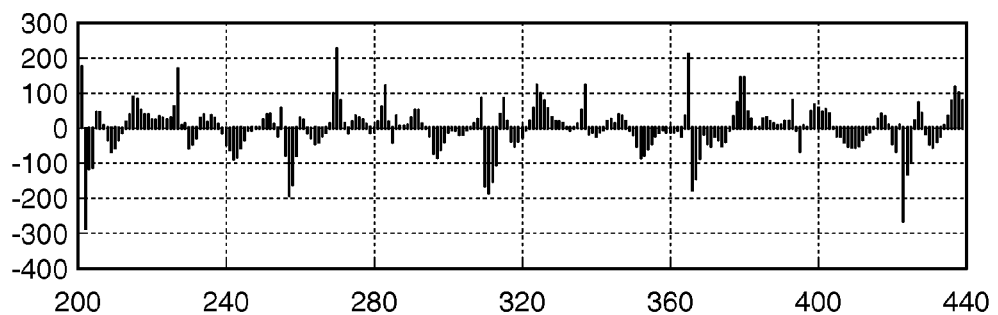
FIGS. 3A-3D are examples of acceleration detection values in the walking state.
Figure 3B:
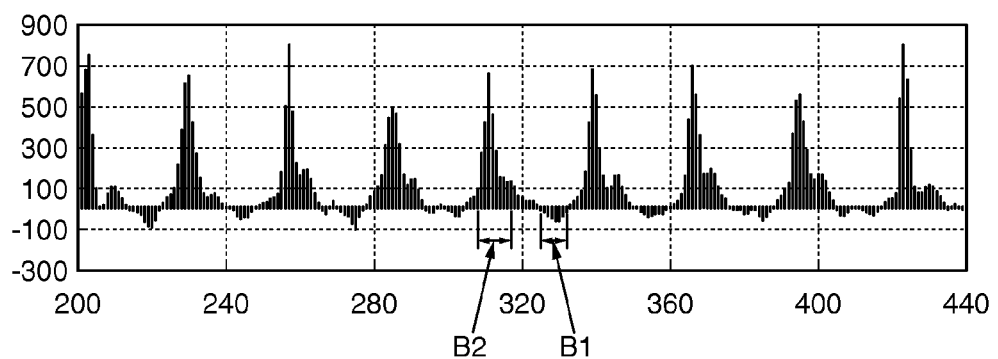
Figure 3C:
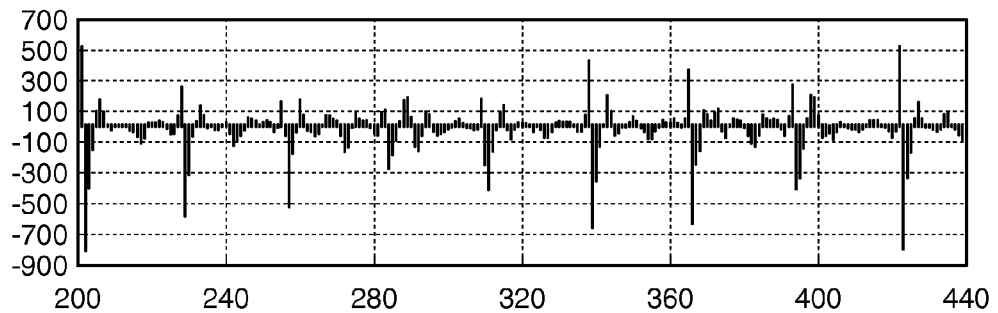
Figure 3D:
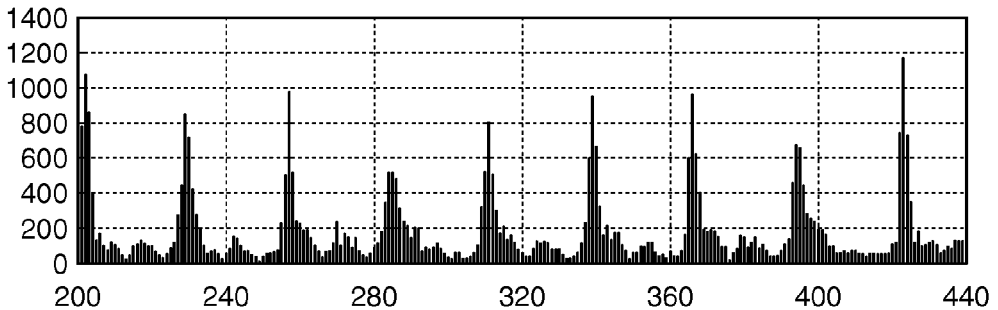

Therefore, according to the first method, a gravity direction judgment period having a predetermined length of time (for example, one second, or the like) is set, and the sign of the direction of gravity (a coordinate axis component of the gravitational acceleration) is specified based on the acceleration detection value in the period. Concretely, the sign of an integrated value of acceleration detection values in the gravity direction judgment period set may be assumed to be the sign of the direction of gravity. As shown in FIG. 3B, acceleration detection values in the coordinate axis used for the processing will mostly have the sign corresponding to the gravitational acceleration, and their values are large, while acceleration with the sign different from that of the direction of gravity appears only for a short time, and their value is small. Therefore, if the length of the gravity direction judgment period is appropriately set, the sign of an integrated value of the acceleration detection values would coincide with the sign that expresses the direction of gravity.

As the gravity direction judgment period, a period that is sufficiently longer than a period in which acceleration in the opposite direction of the direction of gravity appears in one step may be set. When this requirement is not met, there is a possibility that an integration processing is performed in a period where acceleration in the opposite direction is locally predominant, such as, for example, a period indicated by B1 in FIG. 3B, which leads to misjudgment. In this respect, if a period that is sufficiently longer than the period indicated by B1 can be set, the direction of gravity becomes predominant without depending on which timing the gravity direction judgment period is started in each step, such that the possibility of misjudgment can be suppressed. As there is no particular limitation to the upper limit of the length of the gravity direction judgment period from the accuracy point of view, any value that is allowable in the system, in relation to other processings or the like, may be set.

Then, a predetermined walking or running judgment period is set, and a walking or running judgment may be performed through detecting as to whether an acceleration detection value with the sign different from the direction of gravity appears during the walking or running judgment period. Here, the walking or running judgment period may be a period corresponding to the length of one step, if the walking or running judgment wants to be made in every step. Therefore, if the judgment only has to be made every two steps or three steps, the length of two steps or the length of three steps corresponds to the walking or running judgment period.

Figure 8:
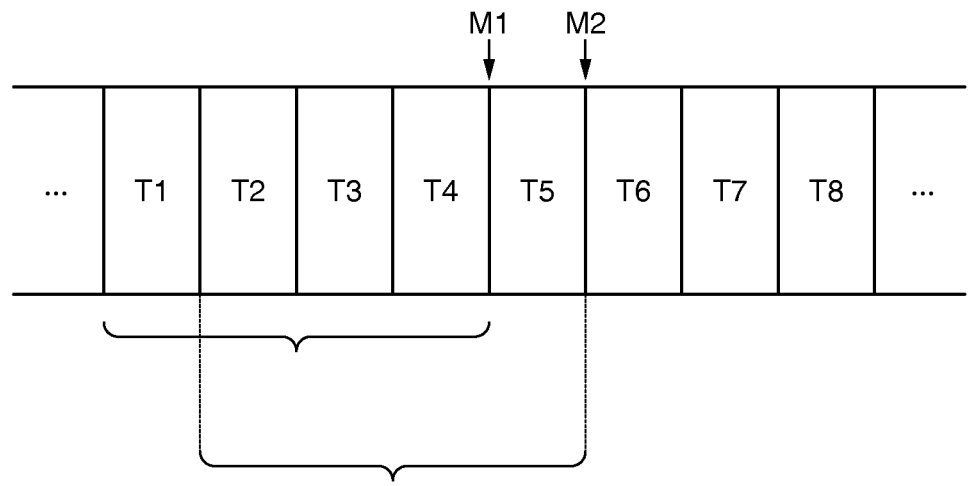
FIG. 8 shows an example of the setting of walking/running judgment periods.

One walking or running judgment period and the next walking or running judgment period may be set in a manner to overlap each other as shown in FIG. 8. Each of T1-T8 of FIG. 8 corresponds to the length of one step, respectively. For instance, T1-T4 may be used for the judgment at M1 (at the time T4 ends), and T2-T5 may be used for the judgment at M2 (at the time T5 ends), whereby the judgment period can be made longer and the judgment result can be output every one step. However, for example, even when the user is in the walking state in T4, if the user is in the running state in either of T1-T3, there is a possibility that the output at M1 may indicate the running state. In other words, even when the running state shifts to the walking state, there is a possibility that a time lag is caused in reflecting in the judgment result, or a short walking state in a valley between running states cannot be detected. Therefore, the aforementioned points should be considered when the walking or running judgment period, as shown in FIG. 8, is set.

Also, it needs to pay attention to the lower limit of the walking or running judgment period, and it may preferably be longer than the length of one step here. There is no meaningful advantage in the walking or running judgment by a unit finer than each one step, and in addition, there is a possibility that an acceleration detection value with the sign different from the direction of gravity does not appear even in the running state if the period is shorter than one step as shown in FIG. 3B. Therefore, when the period indicated at B2 of FIG. 3B is set as the walking or running judgment period, any acceleration detection value with the sign corresponding to the opposite direction does not appear even when the step is made in the running state, which is therefore determined to be the walking state. In other words, as the walking or running judgment period, it is necessary to set a sufficiently long period to the extent that the sign corresponding to the opposite direction securely appears in the running state, and the lower limit thereof is the length of one step.

The timing, the frequency, etc. of the judgment of the direction of gravity can be freely set. For example, when the electronic apparatus 900 is mounted, the direction of gravity may be determined once, and the judgment result may be kept being used while the measurement is continuing thereafter. Or, whenever the walking or running judgment is performed, the direction of gravity may be judged. For instance, the gravity direction judgment period may be set in a manner to overlap a part (for example, the first half portion) of the walking or running judgment period, and the walking or running judgment may be made based on the judgment result as to the direction of gravity. In this case, the walking or running judgment may not be performed in the walking or running judgment period that overlaps the gravity direction judgment period, or data may be maintained and the judgment may be made after the direction of gravity is judged. Additionally, the timing to judge the direction of gravity may be set by various techniques.

By the method described above, the running state is determined when an acceleration detection value with the sign in the opposite direction of the direction of gravity appears, and the walking state is determined when such a value does not appear. However, the embodiment is not limited to the one that outputs the judgment result in one judgment timing as it is. For example, judgment results in multiple times (three times, etc.) may be stored, and those results may be integrated and output as a final output. For example, judgment results in the latest 3 times may be stored, and a decision by majority may be made such that, when the same state is determined twice or three times, that state may be output.

3.3 Second Method

According to the method described above, the sign of the direction of gravity is detected. However, the invention is not limited to the method described above. According to the second method, the walking or running judgment is made based on whether the sign of the acceleration detection value reverses during the walking or running judgment period, and whether the direction of gravity is in the positive direction or in the negative direction is not particularly judged.

As the walking or running judgment period in this embodiment, a period during which reversion of the sign securely appears in the running state may be set, which may be a period longer than the length of one step, similarly to the first method.

In the running state, there are timings at which the sign reverses as shown in FIG. 3B. In the walking state, the sign of acceleration detection values may be positive or negative, but only one of them appears and they do not reverse as shown in FIG. 2B.

Moreover, it is not necessary to consider the case where the sign does no reverse in the running state because the period longer than the length of one step is used for the walking or running judgment as described above. This is because, if only acceleration detection values with a sign that corresponds to the opposite direction of the direction of gravity were to appear in a sufficiently long walking or running judgment period, it means that the user is continuously gaining an upward propulsion force, which is irrational as the movement of a human being.

A processing that combines the judgment results in multiple times (a decision by majority, etc.) may be performed in the second method.

4. Assumption of Speed

Next, a method for assuming the moving speed and the moved distance of the user based on acceleration detection values from the acceleration sensor will be described. The moved distance can be obtained by the number of steps×the pace and the moving speed by the distance/the time required, and even if walking and running can be distinguished from one another, it is not easy to assume accurately the pace from there. In this regard, a method of calculating speed information that does not depend on the number of steps will be described below.

Specifically, a method of obtaining speed information directly from acceleration detection values and a method of obtaining speed information from angle changes in acceleration vectors corresponding to acceleration detection values are described. In this case, it is assumed that the actual acceleration detection values and the angle changes in the acceleration vectors become different in the walking state and in the running state. In other words, because the following methods can reflect differences in the states of movement to some degree, the speed can be relatively accurately assumed, compared with the method based on the pace, even when it is not used with the walking or running judgment of the embodiment.

In light of the above, according to the state detection device 100 in accordance with the present embodiment, the walking or running judgment and the assumption of speed, etc. may be independently performed. However, the speed information calculation processing by the speed information calculation part 130 may be changed based on the result of the walking or running judgment by the judgment part 160. More specifically, parameters, etc. to be used for the speed information calculation processing may be changed according to the state of movement.

Moreover, when the following methods are used, the degree of freedom in the installation position of the acceleration sensor 200 can be increased. Usually, movements of the chest and the waist when walking and running are smaller than those of the leg and the arm. Therefore, when the acceleration sensor 200 is put on these parts, the acceleration detection value also becomes small, and accurate speed assumption becomes difficult. However, the following methods can also accommodate cases where the acceleration sensor 200 is installed on the chest.

4.1 Method Based on Average Value of Acceleration Detection Values

Figure 9:
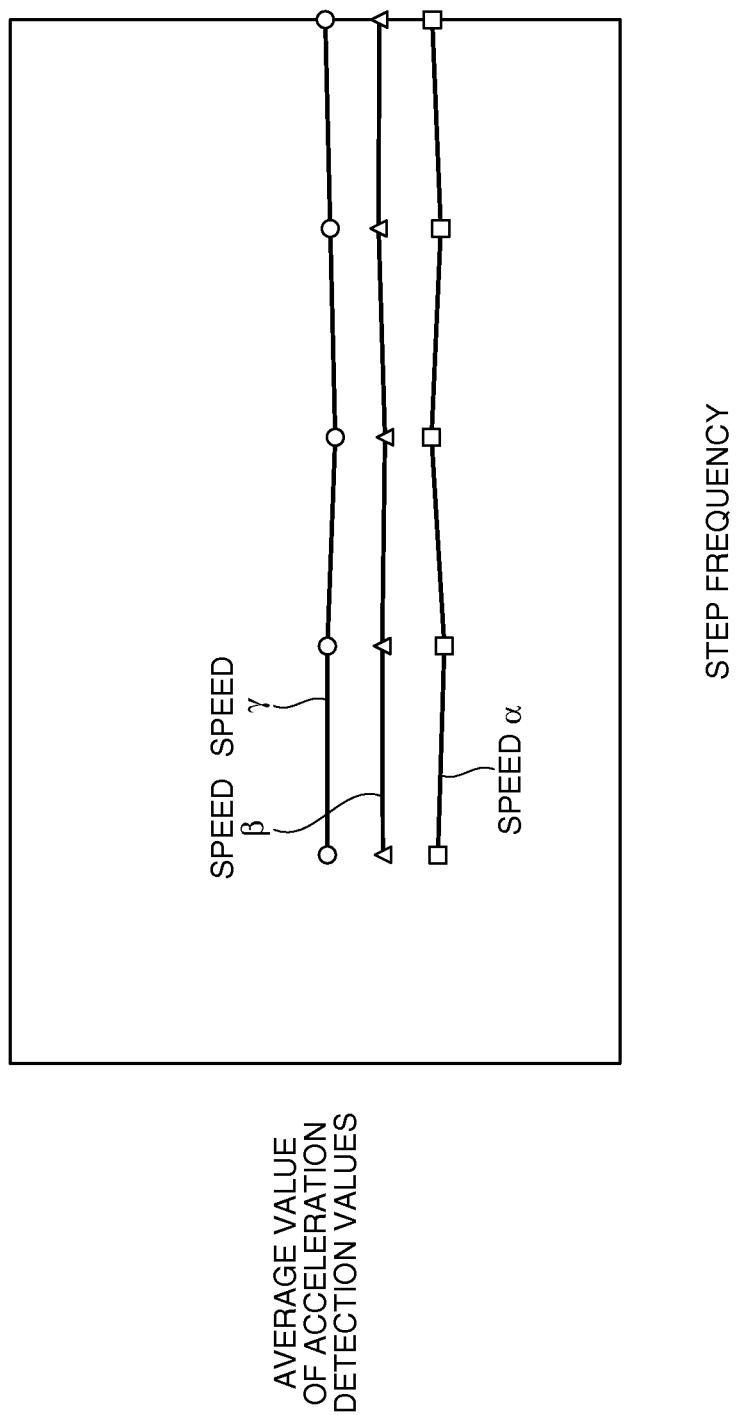
FIG. 9 is a graph showing the relation between average values of acceleration detection values, step frequency and speed.

First, a method based on an average value of acceleration detection values will be described. FIG. 9 shows an example of average values of acceleration detection values, when the walking exercise is carried out in various combinations of the walking pitch (corresponding to the step frequency) and the speed. As is clear from FIG. 9, when the speed is constant, the average value of the acceleration detection values in a predetermined time does not depend on the step frequency and becomes generally a constant value. Also, there is a tendency in that, the greater the speed, the greater the average value of the acceleration detection values becomes.

A variety of methods for calculating an average value of acceleration detection values is possible in this embodiment. As described above, when the acceleration sensor 200 is an acceleration sensor with N axes, the acceleration detection value is an N-dimensional vector. For example, in FIG. 9, the magnitude of an acceleration detection value (the magnitude of a vector) Va is obtained by an expression (3) below, assuming N=3 (three axes of X, Y, and Z), and it is assumed to use an average value of the values Va obtained at specified timings within a predetermined period. Note, however, that the average value of the acceleration detection values may be obtained by a method other than the expression (3) shown below.

[Expression 3]

$$Va = \sqrt{x^2 + y^2 + z^2} \quad (3)$$

It is thought, based on FIG. 9, that there is a strong correlation between the average value of the acceleration detection values and the moving speed. Therefore, once their relation is obtained, speed information can be calculated based on the average value of the acceleration detection values. Here, when the average value of the acceleration detection values is S, and the speed information (the speed itself is assumed here) is T, a linear expression of T=aS+b is assumed. The speed information is calculated by appropriately setting the parameters for speed information calculation a and b.

When multiple users are the subject, general-purpose values that can secure the accuracy to some degree may be set for the values a and b. However, there is a limit in respect of the accuracy in using common parameters because there are individual variations among the users. Therefore, values different for each user may be set according to circumstances, and a calibration processing may be performed for that purpose. Since two unknown numbers, a and b, need to be decided, it is necessary to acquire two different combinations of S and T. For example, this can be accomplished by making the user walk a known distance (100m, for example) at two different speeds, and the information obtained can be used. In this case, S can be acquired from the information from the acceleration sensor 200, and because the user walked a known distance, the speed T can be obtained by dividing the distance by the time required. In other words, two relational expressions for the two unknown numbers a and b can be obtained, such that a and b can be uniquely decided.

Note that the combination of a and b may be changed according to the walking state or the running state. In this case, parameters for walking a1 and b1 are used when walking, and parameters for running a2 and b2 are used when running. In this case, if the calibration is to be performed, it is possible that a1 and b1 may be decided based on two sets of movement at different walking speeds, and a2 and b2 may be decided based on two sets of movement at different running speeds.

4.2 Method Based on Value Corresponding to Absolute Value of Coordinate Axis Component When an average value of the acceleration detection values is used, square root operation is needed as shown in the above expression (3), and further division is needed to obtain the average value, which leads to a problem of substantial computational complexity.

Figure 10:
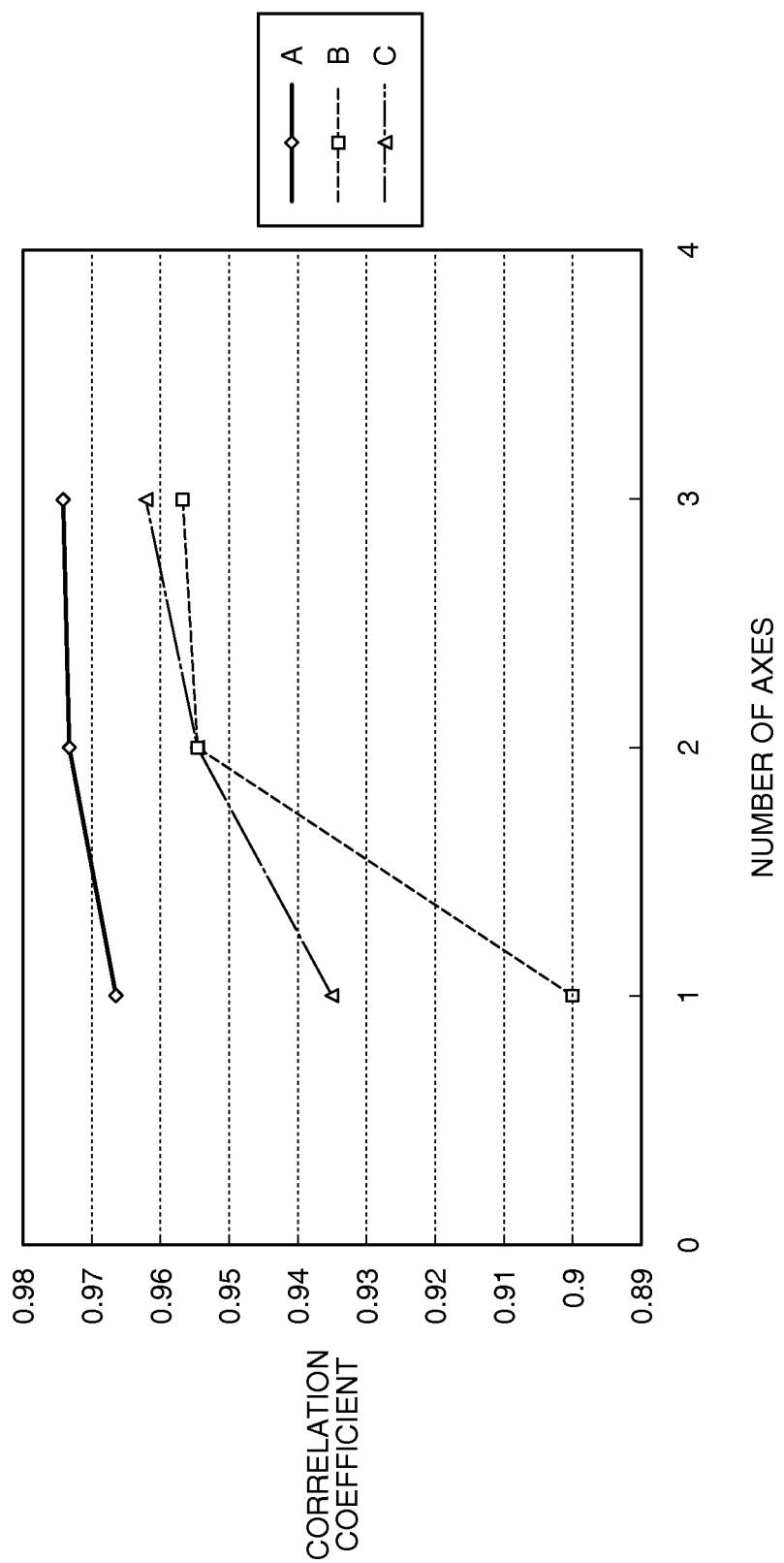
FIG. 10 is a graph showing the relation between the number of axes and correlation coefficient used for calculation of speed information.

Here, a method of calculating speed information that does not involve square root operation and division will be described. Moreover, because speed information can be calculated in this method by using coordinate axis components in one or at least one of a plurality of axes (three axes, for example) of the acceleration sensor 200, it can be expected to further reduce the computational complexity. However, as indicated in FIG. 10, the accuracy increases by increasing the number of axes used for the processing. The correlation coefficients in FIG. 10 express correlation values between the calculated speed information and the actual moving speeds of the user. It is shown that, the greater the correlation coefficient, the more the assumed speed value approximates the actual moving speed of the user. Also, note that A, B, and C show the test results by three different users.

Figure 11:
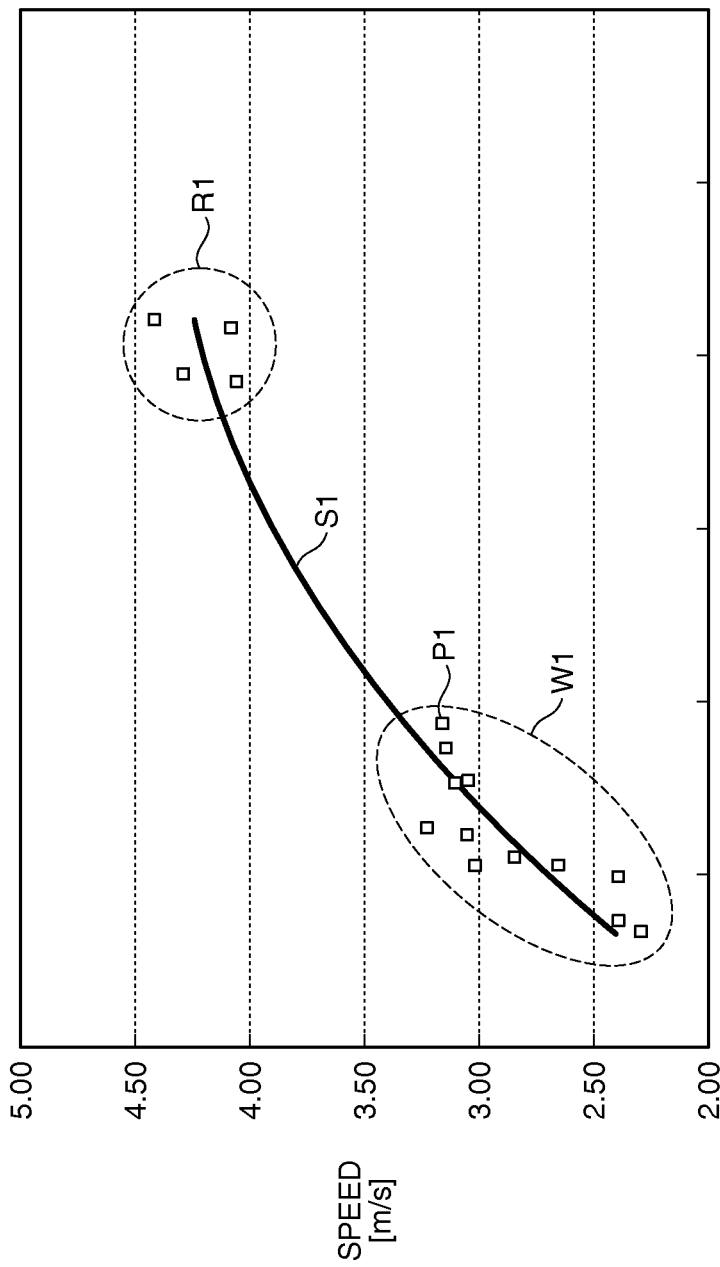
FIG. 11 is a graph showing the relation between integrated values of acceleration detection values and speed information.

The speed information calculation part 130 integrates acceleration detection values in at least one of the coordinate axis components of the acceleration sensor 200 for a predetermined period to obtain an integrated value I. The relation between the integrated values I and speed information is shown in FIG. 11, wherein square dots such as P1 show the results of the measurement. As is clear from FIG. 11, the relation between the values I and speed information can be excellently represented by a curve S1.

Therefore, the speed information r is obtained here according to the relational expression of $r = cI^2 + dI + e$. Here, the speed information r per se may be the speed, or may be information that corresponds to its ratio to a standard speed, or the like. When r is information such as the ratio, etc., the actual speed can be obtained by an expression, for example, $V_d = rV_s$, where $V_s$ is the standard speed and $V_d$ is the assumed speed.

Different values may preferably be set for c, d, and e (and, $V_s$), respectively, according to the number of axes used, and a predetermined period in which the integration processing is performed. In addition, in consideration of the individual variation of each user, values suitable for each user who uses the device may preferably be set. In this case, calibration processing may be performed based on the measured values for the user. Moreover, the values of c, d, and e (and, $V_s$) may be switched according to the state of movement (in particular, the walking state or the running state), similarly to the values a and b described above.

The coordinate axis components of the acceleration detection values are not necessarily, always positive values (or, always negative values). Therefore, when the signs of the first acceleration detection value and the second acceleration detection value which are subject to the integration processing are different from each other, these values are negated each other thereby making the integrated value smaller, so that appropriate speed cannot be assumed. Accordingly, the integration processing may be performed, without using coordinate axis components of the acceleration detection values per se, but using values corresponding to their absolute values. Considering the fact that all the signs subject to integration only have to be consistent (and may include 0) with one another, a value corresponding to the absolute value may be an absolute value of the acceleration detection value per se, or a value obtained by raising the acceleration detection value to an even power which always assumes a non-negative value.

Moreover, when the number of coordinate axes to be used for the processing is reduced (for example, when only one axis is used), the magnitude of the acceleration detection value in the axis needs be large to some degree in order to secure the accuracy of the speed assumption. Especially, when the acceleration sensor 200 is installed on the chest or the waist, acceleration detection values in the horizontal direction become very small. Therefore the coordinate axis to be used for the processing is preferably an axis corresponding to the direction of gravity. In that case, if some deviations from the direction of gravity are allowed (for example, about 45 degrees as described above in the walking or running judgment), it suffices if an axis that is the nearest to the direction of gravity (or, its opposite direction) among the axes of the sensor coordinate system is selected. However, it is required to suppress the deviation from the direction of gravity (or, its opposite direction) as much as possible if greater accuracy is to be achieved, and there is no guarantee that the axes included in the sensor coordinate system meet such requirement. Therefore, in this case, coordinate transformation to an analysis coordinate system may be performed according to circumstances, and one of the axes among the analysis coordinate system that has a deviation from the direction of gravity sufficiently small in view of securing the accuracy may be selected.

Moreover, when the number of coordinate axes to be used for the processing is to be increased, an axis corresponding to the direction of gravity may preferentially be used. The integrated value I in the case of using a plurality of axes may be the sum of integrated values obtained in the respective axes, or may be obtained by another method.

4.3 Method Based on Angle Change of Acceleration Vector

Also, speed information may be calculated, not based on an acceleration detection value, but based on an angle change in an acceleration vector corresponding to the acceleration detection value. Concretely, angle information corresponding to an angle defined between a first acceleration vector corresponding to an acceleration detection value in the first timing and a second acceleration vector corresponding to an acceleration detection value in the second timing is obtained, and speed information is calculated based on the angle information obtained.

Figure 12:
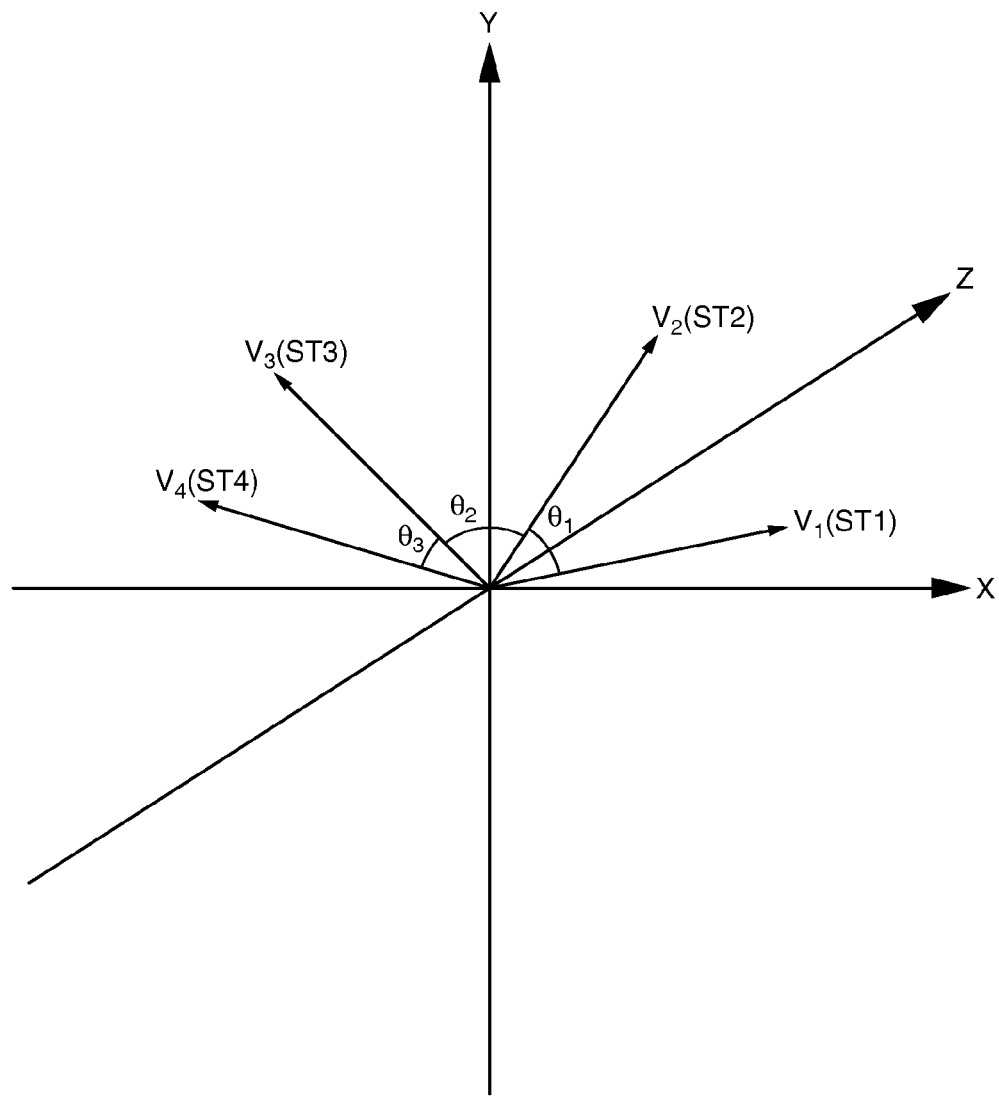
FIG. 12 shows an example of vectors expressed by acceleration detection values and angle information.

When the acceleration sensor 200 is a three-axis acceleration sensor, acceleration detection values correspond to vectors in the three-dimensional space, which are defined as acceleration vectors corresponding to the acceleration detection values. FIG. 12 shows a concrete example of first and second acceleration vectors and their angle information. A corresponding acceleration vector V1 is decided from an acceleration detection value acquired at time ST1, and a corresponding acceleration vector V2 is decided from an acceleration detection value acquired at time ST2. Here, when V1 and V2 are defined respectively as the first acceleration vector and the second acceleration vector, the angle information is an angle defined between V1 and V2. When V1=(x1, y1, z1) and V2=(x2, y2, z2), the angle information θ can be obtained by an expression (4) shown below.

[Expression 4]

$$\theta = \arccos\left(\frac{x_1 x_2 + y_1 y_2 + z_1 z_2}{\sqrt{x_1^2 + y_1^2 + z_1^2}\sqrt{x_2^2 + y_2^2 + z_2^2}}\right) \quad (4)$$

Note, however, that the angle information is not limited to the one expressed above, but may be information mathematically equivalent thereto. For example, a supplementary angle of the angle θ obtained by the above expression (4) may be used as angle information. In this case, the value of angle information or the value of an integrated angle to be described later become grater compared with the case where the angle θ in the above expression (4) is used, and therefore a processing such as a processing to reduce the values of parameters m and n to be described later is needed. Alternatively, an inner product of V1 and V2, or the like may be used as angle information.

The angle information may be information that approximates the angle defined between V1 and V2. For example, the angle information may be obtained as an integer type in the system. If the value of the angle information is expressed by using a floating point number, the angle information can be obtained with good accuracy, but the operation by the floating point number results in a higher processing load. In this respect, the processing load may be reduced by using an index value of the integer type as angle information. Simply, when a value obtained by omitting the figures after the decimal point of the value of an angle defined between V1 and V2 is δ (δ is an integer), δ can be used as the angle information. In this case, however, the angle can be expressed only in the unit of one degree, and therefore an error may be generated between the value of the actual angle and the value expressed by the angle information, which leads to a lowered accuracy in the speed assumption, etc. Therefore, a certain conversion may be performed, and an index value of the integer type of which, for example, 0.5 degrees is set as 1 may be used as angle information. In this case, the index value of 20 will represents 10 degrees, such that the angle can be represented in the unit of 0.5 degrees. Also, the angle information may be any information corresponding to an actual angle, without any particular limitation to the above.

Details of the processing to obtain speed information based on the angle information θ will be described. For example, when the user's body is shaken right to left while moving, it is possible that the user's body may be momentarily accelerated. In this case, if the speed assumption processing is performed only based on angle information obtained at a certain time, speed information may be erroneously assumed to be greater, compared with the case when the user's body is not shaken. Therefore, it can be expected that such an error can be prevented from occurring if not only angle information obtained at a certain time, but also plural angle information sets obtained in a predetermined period are used for the speed assumption processing.

Figure 13:
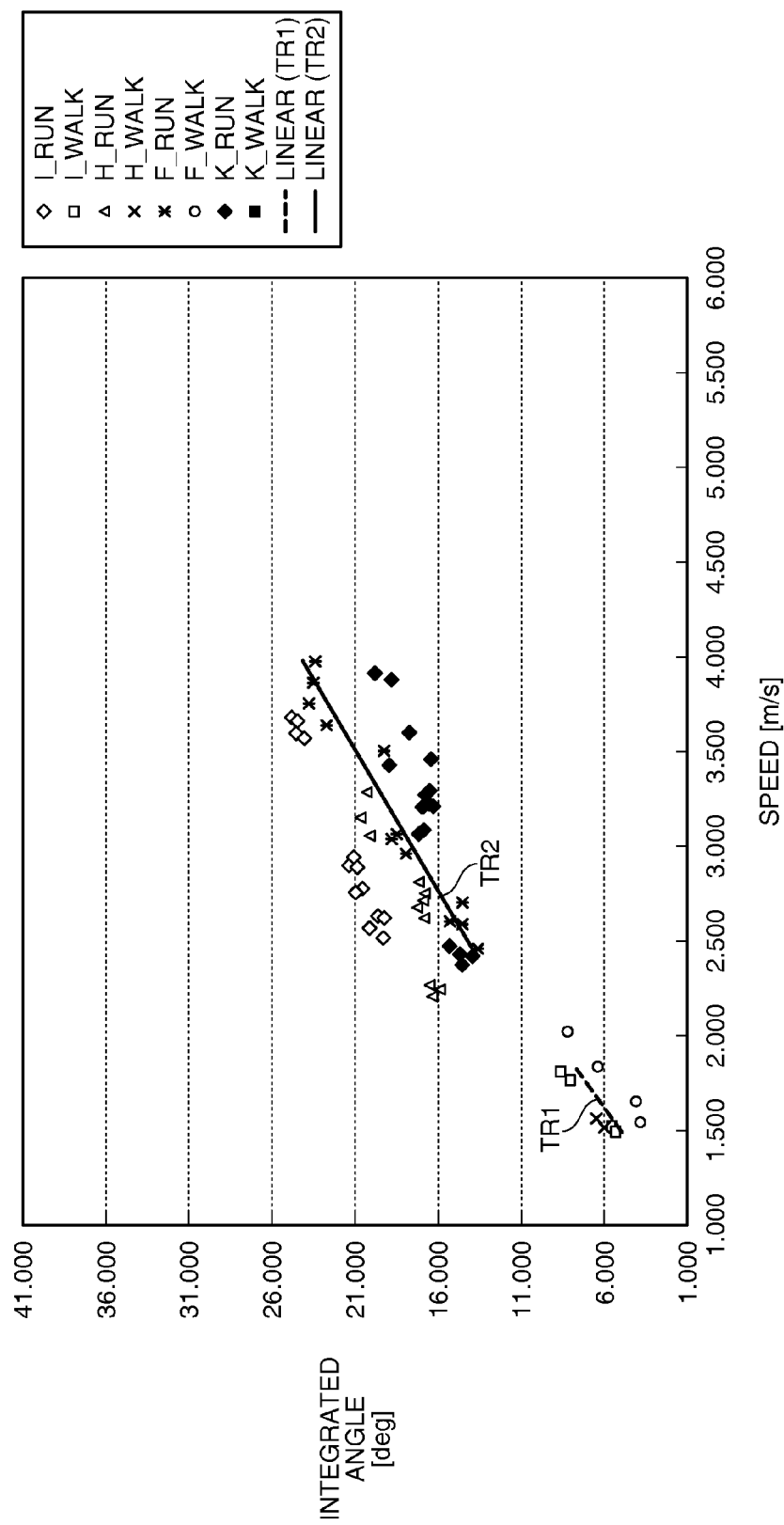
FIG. 13 is a graph showing the relation between integrated angles and speed information.

Accordingly, the speed information calculation part 130 may integrate values each expressed by the angle information θ obtained in the predetermined period to obtain integrated angle $\theta_{sum}$, and speed information V may be obtained from the relational expression of $V = m\theta_{sum} + n$. That the speed information can be expressed by the linear expression of the integrated angle is empirically obtained. A concrete example is shown in FIG. 13. FIG. 13 is a graph showing the relation between integrated angles and measured speed values. Each of sequential data shows data of four testees I, H, F and K when walking (I_WALK, H_WALK, F_WALK, K_WALK) and data when running (I_RUN, H_RUN, F_RUN, K_RUN). As is clear from FIG. 13, when focusing on the user data of one person, the relation between the integrated angles and the speeds in walking is excellently represented by a given linear line, and the relation thereof in running is excellently represented by another linear line different from that in walking. More concretely, a high correlation with correlation coefficients of 0.98-0.99 is obtained.

Note that, as the values m and n, all-purpose values (for example, m and n corresponding to the linear line TR1 in walking and the linear line TR2 in running in FIG. 13) may be used, or different values may be set for each of the users, or the values m and n may be decided through calibration processing based on the actual measured values, similarly to the example described above. As can be understood from FIG. 13, etc., typical values of m and n are different in the walking state and in the running state in this method, and therefore it is preferred to switch the values of m and n depending on the walking state or the running state, based on the judgment result by the judgment part 160.

In the above-described embodiment, the state detection device 100 includes the acquisition part 110 that acquires acceleration detection values from the acceleration sensor 200 and the judgment part 160 that judges the running state or the walking state based on the acceleration detection values, as shown in FIG. 1B. The judgment part 160 judges, in a predetermined judgment period, as to whether the positive or negative sign of the acceleration detection value in the first axis reverses, and determines the running state when the positive or negative sign reverses. Moreover, when the positive or negative sign does not reverse, the judgment part 160 determines the walking state.

The predetermined judgment period is a period in which the walking state and the running state can be discriminated from each other, and according to the present embodiment wherein reversing of the positive or negative sign is observed, it may preferably be a period in which reversing of the sign in the walking state is hardly possible, but the possibility of reversing the sign in the running state is a very high. Note that the predetermined judgment period may be set in the state detection device 100, or may be set from external equipment, or may be a value pre-fixed at the time of manufacturing.

As a result, it is possible to judge the walking state or the running state based on the judgment of the positive or negative sign. In the threshold judgment of related art that uses the step period (i.e., the step frequency), there are problems in that a suitable threshold value varies depending on the user's individual variation, exercising condition, etc., and the possibility of misjudgment in the vicinity of the threshold value becomes higher. Because such processing is made unnecessary in the present embodiment, the judgment accuracy can be improved, compared with the method of related art.

Moreover, the judgment part 160 may judge the running state or the walking state based on the acceleration detection value in an axis in the direction corresponding to the direction of gravity set as the first axis.

As a result, processings based on the direction of gravity become possible. Because, in the embodiment, the walking or running judgment is performed based on whether or not the user comes off the ground (there is a moment when the user is not on the ground), an appropriate judgment can be made by using the direction of gravity as reference. Note that, as described above, the first axis is not limited to the direction of gravity. When a coordinate axis is set, because the coordinate axis component of the gravitational acceleration only has to be sufficiently large, some deviation within a predetermined range from the direction of gravity is permissible, and an axis in the direction or an axis deviated in a predetermined rage from the direction may be used.

Moreover, the judgment part 160 may judge, based on the sign of the acceleration detection value in the first axis, as to whether the sign corresponding to the direction of gravity is positive or negative in the first axis. And, when the acceleration detection value in the first axis with a sign different from the sign corresponding to the direction of gravity is detected at least once during the predetermined judgment period, the running state is determined.

Accordingly, after detecting the sign corresponding to the direction of gravity, when an acceleration detection value with a sign different from the aforementioned sign is acquired, the running state can be determined. As described above, a coordinate axis to be used for the processing is sufficient if it makes the component of the gravitational acceleration predominant, and therefore the aforementioned component of the gravitational acceleration may appear as a positive value or a negative value. In other words, because it is not known as to whether the direction of gravity is positive or negative, it cannot be distinguished by looking at the sign of the acceleration detection value in the judgment period as to whether the sign is in the direction along the direction of gravity or it is in the direction along the opposite direction. Therefore, the sign of the direction of gravity is first determined, and then the processing is carried out based on the determination, whereby the walking or running judgment can be made based on the acceleration detection value in the coordinate axis set according to the reference described above.

Also, when the sign of the acceleration detection value in the first axis in a first period within the predetermined judgment period is positive, and when the sign of the acceleration detection value in the first axis in a second period within the predetermined judgment period following the first period is negative, the judgment part 160 may determine the running state. Alternatively, when the sign of the acceleration detection value in the first axis in the first period is negative, and the sign of the acceleration detection value in the first axis in the second period is positive, the judgment part 160 may determine the running state.

Here, the first period and the second period are included in the judgment period, and the beginning timing of the second period may be simultaneous with or later than the end timing of the first period. Moreover, the union of the first period and the second period may correspond to the judgment period, and the judgment period may include a period that is not included in the first period or the second period.

As a result, the walking or running judgment can be made based on whether or not the sign of the acceleration detection value reversed in the judgment period. Accordingly, the judgment part 160 does not need to recognize as to whether the direction of gravity is positive or negative, whereby the judgment can be made with ease.

Moreover, the judgment part 160 may judge the running state or the walking state based on the acceleration detection value in a period longer than the length of one step in walking or running set as a predetermined judgment period.

As a result, a processing with the judgment period set longer than the length of one step becomes possible. There is no particular restriction to the length of the judgment period in the walking state because reversing of the sign is hardly thinkable no matter what period is set, as shown in FIG. 2B. However, it can be assumed that reversing of the sign of the acceleration detection value from positive to negative or from negative to positive occurs once in each step in the running state. Therefore, there is a possibility that reversing of the sign does not occur even in the running state if a period shorter than the length of one step is set, which is undesirable. Therefore, the judgment period is preferably set longer than the length of one step, whereby the possibility of misjudgment can be suppressed.

Moreover, the state detection device 100 may include the speed information calculation part 130 that calculates speed information in the walking state or in the running state based on the acceleration detection value, as shown in FIG. 1B.

Note here that the speed information may be the speed itself (that may be expressed by such a unit as m/s, for example), or may be other information corresponding to the speed (that may be, for example, a scale factor to a reference speed).

As a result, in addition to the walking or running judgment, calculation of the moving speed of the user becomes possible. Because the situation where the walking or running judgment is made is just a situation where the user is believed to be walking or running, information on the moving speed in that case is useful for the user as it expresses the user's own state.

Moreover, when an average value of acceleration detection values is S, and speed information calculation parameters are a and b, the speed information calculation part 130 may calculate speed information T by T=aS+b.

As a result, calculation of speed information based on an average value of acceleration detection values becomes possible. As the acceleration detection value, vectors with components corresponding to the number of axes of the acceleration sensor 200 are thought to be present. Therefore, a root-sum-square value of the vectors is obtained here as shown in the expression (3), and an average value of the aforementioned values in a predetermined period is used as S. According to this method, the pace assumption that is difficult to accomplish with extreme precision needs not be performed, it can be expected that the accuracy of speed information is improved, compared with the method using the pace.

Also, the speed information calculation part 130 may calculate speed information r by $r=cI^2+dI+e$, where I is an integrated value of values corresponding to absolute values of acceleration detection values in at least one of the coordinate axis components, and c, d and e are speed information calculation parameters.

Note here that the value corresponding to the absolute value may be an absolute value of the subject coordinate axis component per se, or a value obtained by raising the coordinate axis component to an even power. Further, the integrated value may be the sum of values corresponding to absolute values in a period subject to the processing. Also, the integrated value may be obtained by simple addition, or by addition processing after multiplying the values by a coefficient other than 1.

As a result, the computational complexity can be reduced, compared with the case of using average values of acceleration detection values, because speed information can be calculated without performing square root operation or division.

Also, the speed information calculation part 130 may calculate speed information based on angle information θ corresponding to an angle defined by a first acceleration vector that expresses an acceleration detection value at a first timing and a second acceleration vector that expresses an acceleration detection value at a second timing, and parameters for speed information calculation. Concretely, when an integrated value of the angle information θ is $\theta_{sum}$, and the parameters for speed information calculation are m and n, the speed information V may be calculated by $V=m\theta_{sum}+n$.

As a result, speed information can be calculated based on angle information. In this case, because the method does not depend on the number of steps, speed information can be accurately calculated. Note that loci expressed by angle information change for different users, or when the state of movement changes even in the case of the same user. Accordingly, angle information may be used not only for calculating speed information but also for distinguishing users and distinguishing the states of movement.

Moreover, when the running state is determined by the judgment part 160, the speed information calculation part 130 may set a parameter for running as the parameter for speed information calculation. Also, when the walking state is determined by the judgment part 160, the speed information calculation part 130 may set a parameter for walking as the parameter for speed information calculation As a result, the parameter to be used to calculate speed information can be switched according to the walking state or the running state, and therefore the speed information can be accurately calculated, compared with the case where the parameter is not switched.

Moreover, the state detection device 100 may include the distance information calculation part 170 that calculates moved distance information in the walking state or the running state based on speed information calculated by the speed information calculation part 130, as shown in FIG. 1B.

As a result, not only speed information but also distance information that corresponds to the moved distance can be acquired. Note that the distance information is obtained by multiplying the speed information by the length of a period that is subject to calculation of the distance information. If the speed information per se expresses the speed, the distance information per se expresses the distance (that is expressed by such a unit as meter, for example), and if the speed information expresses a scale factor, etc. to a reference speed, the distance information becomes information on the scale factor, etc. to a reference distance.

Moreover, the above-described embodiment is also applicable to an electronic apparatus 900 that includes the state detection device 100 described above and the acceleration sensor 200.

As a result, an apparatus that includes both the state detection device 100 and the acceleration sensor can be achieved. The electronic apparatus 900 may be a heart rate monitor, etc. as shown in FIG. 5A and FIG. 5B, and may be a smart phone, etc. equipped with the acceleration sensor 200.

Figure 7:
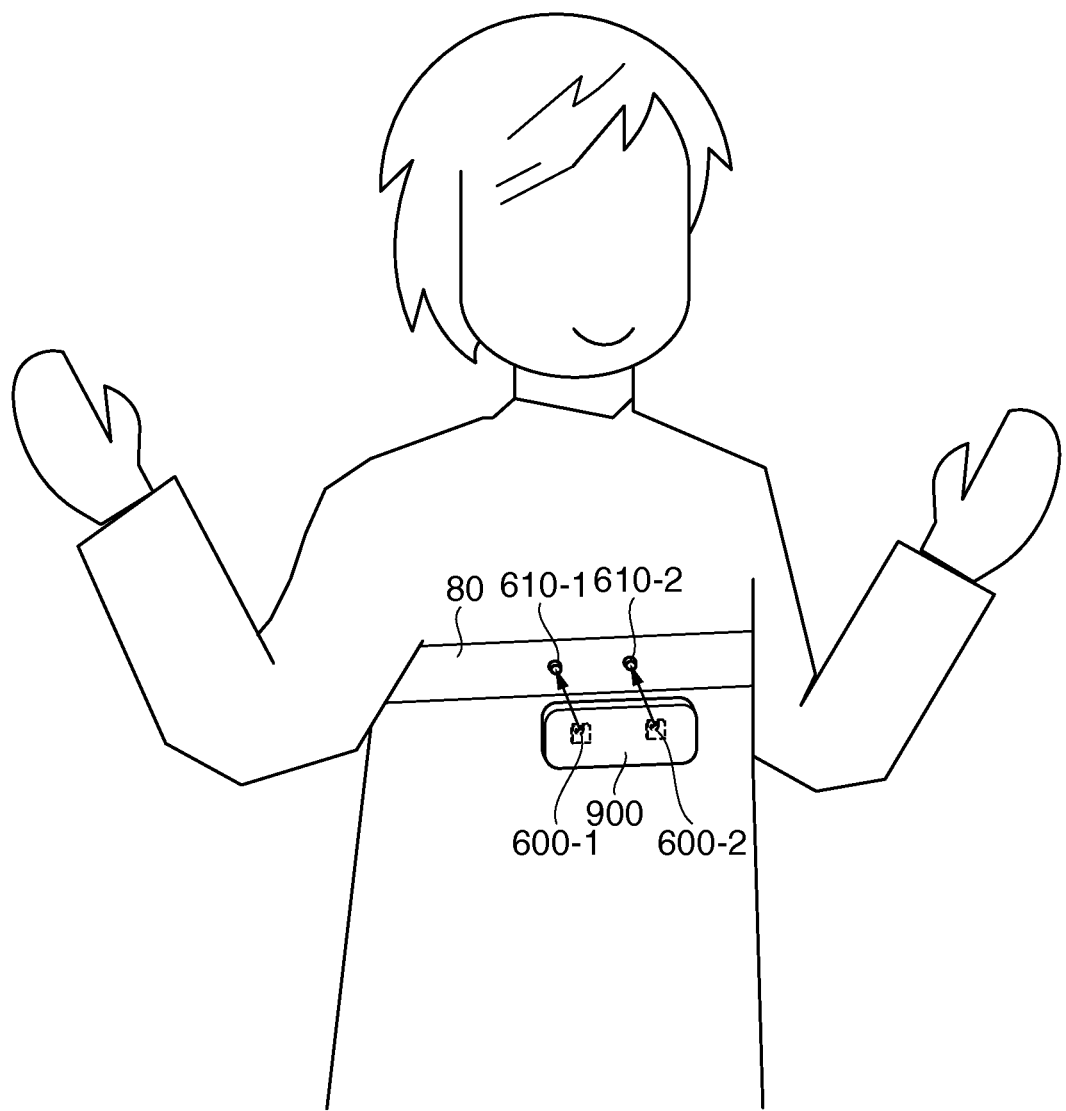
FIG. 7 is an illustration of an example in which an electronic apparatus in accordance with an embodiment is attached to the chest of the user.

The electronic apparatus 900 may include a plurality of terminals (600-1 and 600-2) that are used for detection of heart rates, and affixing the electronic apparatus to the chest of a person to be examined, as shown at FIG. 5B. The acceleration sensor 200 is a three-axis acceleration sensor to acquire acceleration detection values in the mutually orthogonal three axes, X axis, Y axis, and Z axis, as shown in FIG. 5A. Moreover, when the electronic apparatus 900 is affixed to the body to be examined with the plural terminals as shown in FIG. 7, the direction in the Z axis assumes the direction corresponding to the traveling direction in the walking state or the running state. In this case, the judgment part 160 judges the running state or the walking state based on the acceleration detection value in the Y axis.

As a result, the method of the present embodiment can be applied to the heart rate monitor shown in FIGS. 5A and 5B. Because the relative position between the terminals for measurement and the heart is limited in the case of the heart rate monitor to improve the heat rate measurement accuracy, the degree of freedom in its installation attitude with respect to the body to be examined (user) is not high. In particular, in the case shown in FIGS. 5A and 5B, after a specific surface of the heart rate monitor is oriented to the side of the user, the heart rate monitor is supported by two points, such that the attitude of the heart rate monitor can assume only a first attitude and a second attitude to which the up-down direction reverses with respect to the first attitude. Therefore, when a specific axis (Y axis in FIG. 5A) among the axes of the acceleration sensor 200 is made to correspond to the direction of gravity (or, its opposite direction) in the first attitude, the specific axis will correspond to the opposite direction of the direction of gravity (or, the direction of gravity) even when the second attitude is assumed. When realizing the electronic apparatus 900 in a smart phone, a processing for selecting an axis to be used for the processing from among the axes of the acceleration sensor 200 (for example, a processing based on the angle and the acceleration detection value) is necessary in related art. However, according to the present embodiment, a specific axis decided at the time of designing or manufacturing can be used as is without the axis selection processing, and therefore the processing load can be alleviated.

Further, the present embodiment is also applicable to a measurement system that includes the state detection device described above.

As a result, a measurement system that performs the processings of the present embodiment can be achieved. In this measurement system, the state detection device 100 does not need to be installed at a position spatially close to the acceleration sensor 200 or to the user. For example, the user needs only to put on a device that includes the acceleration sensor 200 and a communication unit that transmits acceleration detection values from the acceleration sensor 200 to a network, and other equipment may not be considered. In this case, the state detection device 100 may be realized by another system (for example, by a PC, a server system, or a server system composed of plural servers) that is connected to the network. Because the processing result is generally presented to the user, it may be linked with a system that has a display device, etc. If the user can go in front of the system that corresponds to the state detection device 100 (for example, in the case of a PC installed in a resting place provided as an annex to a playground serving as the state detection device 100), the display device of the system may be used. Moreover, if the state detection device 100 is a server system, a display device of a client device that transmits a request to the server system, and acquires a processing result as a response may be used. A variety of such client devices is possible, and the client device may be a PC. For confirming information while the user is in movements, the client device may be a smart phone, or other devices that can be put on easily, such as, a wristwatch type device, a head-mount display, etc.

A part or a majority of the processings of the state detection device 100, etc. in accordance with the present embodiment may be realized by a program. In this case, a processor such as a CPU executes the program, whereby the state detection device 100, etc., of the embodiment are realized. Concretely, the program stored in an information storage medium is read, and a processor such as a CPU executes the program read out. Here, the information storage medium (e.g., a computer-readable medium) stores programs and data, and its function can be achieved by an optical disk (a DVD, a CD, etc.), a HDD (a hard disk drive) or a memory (a card type memory, a ROM, etc.) and the like. Then, the processor such as a CPU performs various processings according to the present embodiment based on the program (data) stored in the information storage medium. In other words, the information storage medium stores programs to render a computer (a device that has an operation part, a processing part, a storage part, and an output part) to function as each of the parts of the embodiment (in other words, programs that render the computer to execute the processing of each of the parts).

The embodiments of the invention are described above in detail. However, those skilled in the art should readily understand that many modifications can be made without departing in substance from the novel matter and effects of the invention. Accordingly, all of those modified examples are deemed to be included in the scope of the invention. For example, throughout the specification and the drawings, terms described at least once with different terms in a broader sense or synonymous can be replaced with those different terms in any sections of the specification and the drawings. Moreover, the composition and the operation of the state detection device, the electronic apparatus, the measurement system, etc. are not limited to those described by the embodiment, and various modifications can be implemented.

What is claimed is:

1. A state detection device comprising:
an acquisition part that acquires an acceleration detection value from an acceleration sensor; and
a judgment part that judges a running state or a walking state based on the acceleration detection value,
the judgment part detecting as to whether a positive/negative sign of the acceleration detection value in a first axis reversed in a predetermined judgment period,
determining the running state when the sign reverses, and determining the walking state when the sign does not reverse.

2. A state detection device according to claim 1, wherein the judgment part judges the running state or the walking state based on the acceleration detection value in an axis in a direction corresponding to the direction of gravity set as the first axis.

3. A state detection device according to claim 2, wherein the judgment part judges, based on the acceleration detection value in the first axis, if the sign corresponding to the direction of gravity in the first axis is positive or negative,
the judgment part determining the running state when the acceleration detection value in the first axis with the sign different from the sign corresponding to the direction of gravity is detected at least once in the predetermined judgment period.

4. A state detection device according to claim 1, wherein the judgment part determines the running state, when the sign of the acceleration detection value in the first axis in a first period within the predetermined judgment period is positive, and the sign of the acceleration detection value in the first axis in a second period following the first period within the predetermined judgment period is negative, or when the sign of the acceleration detection value in the first axis in the first period is negative, and the sign of the acceleration detection value in the first axis in the second period is positive.

5. A state detection device according to claim 1, wherein the judgment part judges the running state or the walking state based on the acceleration detection value in a period longer than the length of one step in walking or running set as the predetermined judgment period.

6. A state detection device according to claim 1, comprising a speed information calculation part that calculates speed information in the walking state or the running state based on the acceleration detection value.

7. A state detection device according to claim 6, wherein the speed information calculation calculates the speed information T by T=aS+b, where S is an average value of magnitudes of the acceleration detection value, and a and b are parameters for speed information calculation.

8. A state detection device according to claim 7, wherein, the speed information calculation part sets a parameter for running as the speed information calculation parameter when the running state is determined by the judgment part, and sets a parameter for walking as the speed information calculation parameter when the walking state is determined by the judgment part.

9. A state detection device according to claim 6, wherein the speed information calculation part calculates the speed information r by $r=cI^2+dI+e$, where I is an integrated value of values corresponding to absolute values of the acceleration detection values in at least one coordinate axis component, and c, d and e are parameters for speed information calculation.

10. A state detection device according to claim 6, wherein the speed information calculation part calculates the speed information based on angle information θ that corresponds to an angle defined by a first acceleration vector expressing the acceleration detection value at a first timing and a second acceleration vector expressing the acceleration detection value at a second timing, and speed information calculation parameters.

11. A state detection device according to claim 10, wherein the speed information calculation part calculates the speed information V by $V=m\,\theta_{sum}+n$, where $\theta_{sum}$ is an integrated value of the angle information θ, and m and n are the speed information calculation parameters.

12. A state detection device according to claim 6, comprising a distance information calculation part that calculates moved distance information in the walking state or the running state based on the speed information calculated by the speed information calculation part.

13. An electronic apparatus comprising the state detection device recited in claim 1 and the acceleration sensor.

14. An electronic apparatus according to claim 13, comprising:

a plurality of terminals used for detection of heart rate and for attachment of the electronic apparatus to the chest of a body to be examined, the acceleration sensor being a three-axis acceleration sensor that acquires the acceleration detection values along three axes of X axis, Y axis and Z axis that are orthogonal to one another, when the electronic equipment is fixed to the body to be examined with the plural terminals, the direction in the Z axis assuming a direction corresponding to the traveling direction in the walking state or the running state, and the judgment part judging the running state or the walking state based on the acceleration detection value in the Y axis.

15. A measurement system comprising the state detection device recited in claim 1.

16. A program that renders a computer to function as an acquisition part that acquires an acceleration detection value from an acceleration sensor, and a judgment part that judges a running state or a walking state based on the acceleration detection value, the judgment part detecting as to whether a positive/negative sign of the acceleration detection value in a first axis reversed in a predetermined judgment period, the judgment part judging the running state when the sign reversed, and judging the walking state when the sign did not reverse.

* * * * *